United States Patent
Baba et al.

(10) Patent No.: US 8,287,500 B2
(45) Date of Patent: Oct. 16, 2012

(54) ADMINISTRATION INSTRUMENT FOR MEDICAL USE

(75) Inventors: Tokumi Baba, Tokushima (JP); Tokumi Ishikawa, Tokushima (JP); Kouichi Matsuda, Nihama (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/904,508

(22) Filed: Oct. 14, 2010

(65) Prior Publication Data

US 2011/0028906 A1    Feb. 3, 2011

Related U.S. Application Data

(62) Division of application No. 10/498,091, filed as application No. PCT/JP02/13055 on Dec. 13, 2001, now Pat. No. 7,922,699.

(30) Foreign Application Priority Data

Dec. 13, 2001 (JP) ................................. 2001-380023
Dec. 13, 2001 (JP) ................................. 2001-380024
Dec. 13, 2001 (JP) ................................. 2001-380025
Dec. 13, 2001 (JP) ................................. 2001-380026
Feb. 8, 2002 (JP) ................................. 2002-032087

(51) Int. Cl.
*A61M 5/00* (2006.01)
*A61M 1/00* (2006.01)

(52) U.S. Cl. ......................................... 604/187; 604/122

(58) Field of Classification Search .................. 604/187, 604/137, 122, 123, 124, 125
See application file for complete search history.

(56) References Cited

U.S. PATENT DOCUMENTS

| | | |
|---|---|---|
| 3,494,358 A | 2/1970 | Duesterheft et al. |
| 3,557,787 A | 1/1971 | Cohen |
| 4,529,401 A | 7/1985 | Leslie et al. |
| 4,581,022 A | 4/1986 | Leonard et al. |
| 5,034,003 A | 7/1991 | Denance |

(Continued)

FOREIGN PATENT DOCUMENTS

DE    196 47 529    5/1998

(Continued)

OTHER PUBLICATIONS

European Search Report issued Mar. 16, 2011 in corresponding European Application No. 10 19 6861.

(Continued)

*Primary Examiner* — Nicholas Lucchesi
*Assistant Examiner* — Brooke Matney
(74) *Attorney, Agent, or Firm* — Wenderoth, Lind & Ponack, L.L.P.

(57) ABSTRACT

An administration instrument for medical use that can perform injection of a drug solution with stability and with great reliability. For example, at administration, it is possible to prevent a force that presses the injection button from acting in a direction of inserting the needle that is inserted into the skin deeper, and enables the administration under a stable state where the needle does not wobble, thereby alleviating physical and mental pain of the administration patient. With a structure in which an injection button is pressed at an angle that is not parallel to the needle with respect to a direction in which the needle is inserted into the skin, it is possible to prevent the force of pressing the injection button from being transmitted in a direction of inserting the needle into the skin deeper than the initial insertion of the needle, thereby achieving an administration under a stable state.

6 Claims, 16 Drawing Sheets

U.S. PATENT DOCUMENTS

| | | | |
|---|---|---|---|
| 5,259,732 A | 11/1993 | Stern | |
| 5,383,865 A | 1/1995 | Michel | |
| 5,435,645 A | 7/1995 | Faccioli et al. | |
| 5,549,561 A | 8/1996 | Hjertman | |
| 5,569,192 A | 10/1996 | Van Der Wal | |
| 5,593,390 A * | 1/1997 | Castellano et al. | 604/187 |
| 5,628,309 A | 5/1997 | Brown | |
| 5,653,698 A | 8/1997 | Niedospial et al. | |
| 5,742,519 A | 4/1998 | McClendon et al. | |
| 5,782,805 A | 7/1998 | Meinzer et al. | |
| 5,868,710 A | 2/1999 | Battiato et al. | |
| 5,876,380 A | 3/1999 | Manganini et al. | |
| 6,126,646 A | 10/2000 | Hansen et al. | |
| 6,171,276 B1 | 1/2001 | Lippe et al. | |
| 6,277,099 B1 | 8/2001 | Strowe et al. | |
| 6,547,755 B1 | 4/2003 | Lippe et al. | |

FOREIGN PATENT DOCUMENTS

| | | |
|---|---|---|
| EP | 0 615 762 A1 | 9/1994 |
| EP | 1 074 273 | 2/2001 |
| EP | 1 095 668 | 5/2001 |
| FR | 2 535 206 | 5/1984 |
| JP | 59-131361 | 7/1984 |
| JP | 4-312469 | 11/1992 |
| JP | 6-7443 | 1/1994 |
| JP | 6-296691 | 10/1994 |
| JP | 11-267206 | 10/1999 |
| JP | 11-276583 | 10/1999 |
| JP | 2001-46498 | 2/2001 |
| JP | 2001-505104 | 4/2001 |
| JP | 2001-513371 | 9/2001 |
| JP | 2001-340454 | 12/2001 |
| WO | 93/20867 | 10/1993 |
| WO | 98/22168 | 5/1998 |
| WO | 98/26823 | 6/1998 |
| WO | 99/07425 | 2/1999 |
| WO | 00/09184 | 2/2000 |
| WO | 00/69488 | 11/2000 |
| WO | 01/26710 | 4/2001 |
| WO | 01/74421 | 10/2001 |
| WO | 02/07802 | 1/2002 |

OTHER PUBLICATIONS

European Search Report issued Mar. 18, 2011 in corresponding European Application No. 10 19 6856.

Supplementary European Search Report issued Mar. 1, 2010 in European Application No. 02788812.2.

European Search Report issued Aug. 10, 2011 in corresponding European Application No. 10 19 6859.

European Search Report issued Aug. 10, 2011 in corresponding European Application No. 10 19 6864.

* cited by examiner

Fig.16
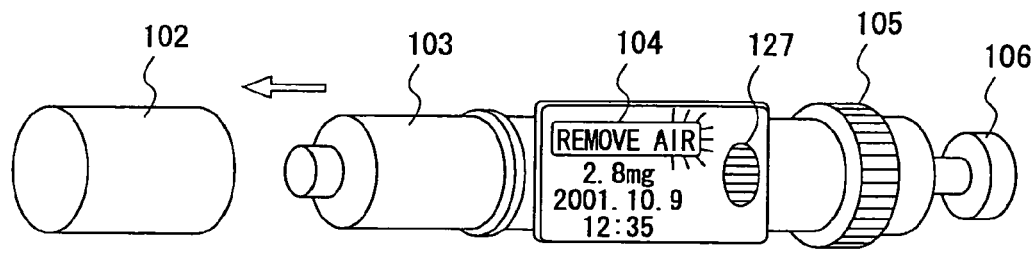
Fig.17
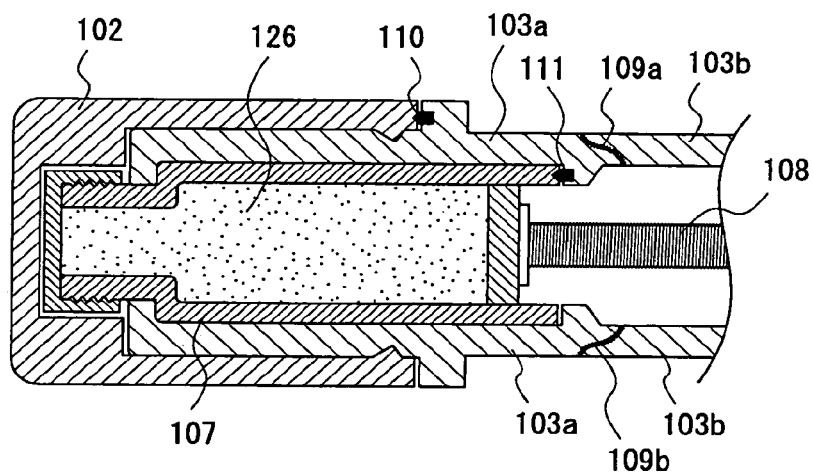
Fig.18

ADMINISTRATION INSTRUMENT FOR MEDICAL USE

CROSS-REFERENCE TO RELATED APPLICATION

This application is a divisional of U.S. application Ser. No. 10/498,091, filed on Jun. 10, 2004 now U.S. Pat. No. 7,922,699, which is a National Stage application of PCT/JP02/13055, filed on Dec. 13, 2001, the entirety of both of which are incorporated herein by reference.

BACKGROUND OF THE INVENTION

I. Technical Field

The present invention relates to administration instruments for medical use, which are used to administer drug solutions such as insulin.

II. Description of the Related Art

Conventionally, administration instruments for medical use have frequently been used in administering drug solutions such as insulin or hormone preparations. Generally, such administration instrument for medical use includes a needle, a syringe body, and an injection button, which are almost aligned, thereby pushing an injection out of a drug solution cartridge that is housed in the syringe body in a direction that is parallel to the needle by means of the injection button. FIGS. 24 and 25 show two typical prior arts.

In FIG. 24, reference numeral 201 denotes a body of an administration instrument for medical use (hereinafter, also referred to as a syringe body), numeral 202 denotes an injection that is sucked in the body 201 of the administration instrument for medical use, numeral 203 denotes an injection button, numeral 204 denotes a needle, and numeral 205 denotes a plunger of a part that is connected to the injection button 203 and directly pushes the injection 202 out of the syringe.

The syringe body 201 contains the injection 202. When the injection is to be administered, the needle 204 is inserted to the skin, and the injection button 203 is pressed, thereby forcing the injection 202 out of the body 201 of the administration instrument for medical use. The amount of the injection 202 administered is decided by adjusting the amount of press onto the injection button 203.

That is, an administrator (patient) pushes the injection button 203 to move the internal plunger 205, thereby forcing the injection 202 out of the needle 204. The amount of sliding of the plunger 205 will decide the amount of the injection that is administered. The administrator (patient) decides the amount of the injection 202 to be administered, inserts the needle 204 into a desired position on the skin, and presses the injection button 203, thereby completing the injection. When the needle 204 is inserted into the skin, the administrator (patient) must decide the amount of the insertion of the needle into the skin based on his/her past experiences or the like.

Most of the administration instruments for medical use that are used for self-administration are mechanical or pen types as shown in FIG. 24. Since the injection button is pushed in the same direction as the initial insertion of the needle into the skin in such instruments, the state of the administration becomes unstable. On the other hand, as shown in FIG. 25, to solve the above-mentioned problem, recently contrived is an administration instrument for medical use including a portion which touches the skin at the administration near the needle, thereby deciding the positions of the needle and the skin to provide the stability of administration.

In FIG. 25, numeral 301 denotes a body of the administration instrument for medical use, numeral 303 denotes an injection button, numeral 304 denotes a needle, numeral 306 denotes a skin touch portion that is touched on the skin in administrating an injection using this conventional administration instrument for medical use, numeral 307 denotes a drug solution cartridge, and numeral 302 denotes an injection in the drug solution cartridge 307.

At the administration, the needle 304 is inserted into the skin with the skin touch portion 306 touched on the skin, and the injection button 303 is pressed to force the injection 302 out of the drug solution cartridge 307. The amount of the administration is decided by adjusting the amount of pressing onto the injection button 303.

In most cases of the conventional administration instrument for medical use, the needle is attached to the instrument body immediately before the actual administration of the injection, and a decided amount of a drug solution is administered to a human body after performing preliminary pressing (hereinafter, also referred to as air removal) to prevent air from being injected with the injection.

In the conventional administration instrument for medical use, the external view of which is shown in FIG. 24, when administering the drug solution, it is possible to push the injection button or the administration button also in a state where the needle is not attached to the administration instrument body. Accordingly, the injection button or the administration button may be inadvertently pushed, thereby causing a problem.

Further, in the case of the conventional administration instrument for medical use, a doctor conducts a diagnosis to give instructions as to the amount of an injection to be administered and the interval of the administration, and the administrator performs self-administration of the drug solution in accordance with these instructions, while management of the amount of the injection administered and the interval of the administration is left to the administrator himself/herself. In addition, the doctor regularly conducts the diagnosis, and newly decides the amount of the injection to be administered and the interval of the administration on the basis of the result of the diagnosis, the amount of the injection that was administered, and the interval of the administration, thereby giving a new instruction.

Conventionally, the mechanical administration instruments for medical use as shown in FIGS. 24 and 25 have been often used for the self-administration, while some instruments that are provided with electronic devices are recently contrived.

A typical structure of this instrument is shown in FIGS. 26 and 27. Further, FIG. 28 shows a block diagram with a microprocessor being shown in the center. FIG. 26 is a front view of the instrument, and FIG. 27 is a top view thereof partially illustrating in cross section.

In FIG. 26, numeral 403 denotes a syringe body, numeral 401 denotes a needle, numeral 404 denotes a display section, numeral 405 denotes a dial for setting the amount of an injection to be administered, and numeral 406 denotes an injection button.

In FIG. 27, a cartridge 407 containing an injection 426 is placed in the syringe body 403. The administrator pulls out the injection button 406 before the injection. When the injection button 406 is pulled out, a sleeve 418 and a nut 412 also slide together with the injection button 406 in the same direction as the injection button 406.

By the sliding of the sleeve 418, a spline portion 416 of the sleeve 418 is coupled to a spline portion 417 of the administration amount setting dial 405. The coupled portion of the sleeve 418 and the plunger 408 is not fixed in the sliding direction but fixed in the rotational direction. The coupled portion of the sleeve 418 and the nut 412 is not fixed in the rotational direction but fixed in the sliding direction.

As a result, when the administrator rotates the administration amount setting dial 405, the sleeve 418 is rotated, and the plunger 408 is accordingly rotated, whereby the plunger 408 is slid by a thread that is provided on the inner circumference of the nut 412 and a thread that is provided on the outer circumference of the plunger 408. The amount of the injection to be administered is decided depending on the amount of the sliding of the plunger 408. When the injection button 406 is not pulled out, the sleeve 418 and the administration amount setting dial 405 are not coupled, whereby even when the administration amount setting dial 405 is rotated, the plunger 408 will never move.

The administrator rotates the administration amount setting dial 405 to decide the amount of the injection to be administered, insets the needle 401 in a position where the administration is to be performed, and then depresses the injection button 406, thereby completing the injection. When the injection has been completed, the injection button 406, the sleeve 418, and the nut 412 are slid in a direction in which they are depressed. In order to detect that the injection button 406, the sleeve 418, and the nut 412 have been slid, a projection 420 is provided on the sleeve 418, and a switch 413 that is turned on or off by the projection 420 is fixed on the body 403.

The switch 413 is turned on when the injection button 406 is pulled out, while the switch is turned off when the injection button 406 is depressed. The completion of the injection is detected by observing the state of the switch 413. As a means for judging the completion of the injection according to the state of the switch 413, a microprocessor 425 as shown in FIG. 28 or the like is employed, and the completion is judged by judging a conduction state of the switch 413.

Here, numeral 417 denotes a spline portion of the setting dial 405, numeral 419a and 419b denote optical sensors, numeral 414 denotes a liquid crystal display, numeral 415 denotes a board, numeral 421 denotes a rotational plate, and numeral 421a denotes a rotational plate slit. In FIG. 28, numeral 422 denotes a memory of the microprocessor 425, numeral 423 denotes a calendar, numeral 424 denotes a clock, and numeral 404 denotes a display interface with the liquid crystal display 414.

FIG. 29 is an enlarged view illustrating a part for detecting completion of the injection. When the amount of the injection administered is to be set, the administration amount setting dial 405 and the sleeve 418 are rotated. The amount of the injection administered is decided depending on the amount of motion of the plunger 408, which is caused by rotation of the administration amount setting dial 405. Therefore, a method is employed in which the amount of the injection administered is detected by detecting the rotation of the administration amount setting dial 405 and the sleeve 418, and the amount of the rotation. Here, numeral 416 denotes a sleeve spline portion, and numeral 417 denotes a setting dial spline portion.

For example, as shown in FIG. 30, the rotational plate 421 that rotates together with the administration amount setting dial 405 is provided, and the slits 421a are formed on the rotational plate 421 as shown in FIG. 31, and two optical sensors 419a and 419b are provided at positions where light crosses the slits 421a. When the administration amount setting dial 405 is rotated, the rotational plate 421 is also rotated, and the slits 421a that are provided on the rotational plate 421 pass through or interrupt the light of the optical sensors 419a and 419b. Since the optical sensors 419a and 419b output an ON signal or an OFF signal depending on the amount of light, it is possible to detect the rotation and the amount of the rotation in accordance with the ON or OFF signal outputted from the optical sensors 419a and 419b.

Here, the reason why two optical sensors 419a and 419b are employed is because the amount of the injection administered is increased or decreased according to the direction of the rotation of the administration amount setting dial 405. The rotation direction is judged on the basis of a phase difference of ON or OFF of the outputs from the two optical sensors 419a and 419b, and the amount of the injection to be administered is detected by counting the number of ON or OFF of the outputs from the optical sensors 419a and 419b. As described above, the microprocessor 425 or the like is employed as shown in FIG. 32 as the means of judging the rotation direction based on the phase difference of the outputs from the optical sensors 419a and 419b, and detecting the amount of the injection to be administered by counting the number of ON or OFF of the outputs from the optical sensors 419a and 419b.

Further, by providing the microprocessor 425 and the memory 422, recording or display of the time and date of the completion of the injection is also performed. In addition, as the optical sensors 419a and 419b, sensors that utilize a switch or the like are contrived.

However, in the conventional administration instrument as shown in FIG. 24, since the needle 204 is inserted into the skin at the administration, and the injection 202 is administered with pressing the injection button 203 in the same direction as that of the insertion of the needle 204 into the skin, the needle 204 would be inserted deeper into the skin from the state where the needle is initially inserted into the skin, thereby increasing the pain of the patient at the administration.

Further, also at the administration in a case where the administration instrument for medical use is provided with the skin touch portion 306 as shown in FIG. 25, the needle 304 is inserted into the skin with the skin touch portion 306 touched on the skin, and then the injection 302 is administered by pressing the injection button 303 in the same direction as the insertion of the needle 304 into the skin. Therefore, also in this case, the above-mentioned problem that the needle 304 would be inserted into the skin deeper from the state where the needle is initially inserted into the skin occurs because, even when the skin touch portion 306 is provided, the actual skin has the elasticity and thus the needle 304 would be inserted into the skin deeper by a force of the actual pressing of the injection button 303.

To avoid this problem, it is necessary to fix the arm by which the injection button 303 is pressed in midair or by some method with care during the administration. However, it is quite difficult when the administration of the drug solution is performed by the patient himself/herself.

When the needle is inserted into the skin deeper during the administration, the pain of the patient would be increased, which is not only distressing both physically and mentally but in some cases may exert many influences upon the body of the administrator (patient), resulting in a hazardous condition to his/her life.

Further, in the conventional administration instrument for medical use as shown in FIG. 24 or 25, since the needle is not always uniform and the length of the needle is different depending on the type, the amount of the needle that is inserted into the skin varies and, in some cases, the failure of the injection or the burden of pain becomes large, and serious influences may be exerted upon the body of the administrator (patient), resulting in a hazardous condition to the life.

Further, in the conventional administration instrument for medical use as shown in FIG. 24, it is possible to press the injection button or the administration button even when the administrator forgets about attaching the needle to the administration instrument body. Therefore, following problems arise.

One of the problems is as follows. When the injection button or the administration button is pressed without the needle attached, the drug solution may be leaked out of the end portion of the syringe opposite to the injection button or the administration button or the drug solution may flow backward and leak toward the injection button or the administration button, like a leaking drug solution 221a or a backward flowing drug solution 221b in FIG. 33, or, as shown in FIG. 34, the glass tube itself containing the drug solution obtains cracks 227 or is ruptured due to a force that is generated by the pressing of the injection button or the administration button, and broken, whereby the drug solution leaks outside.

Further, also in cases where two types of drug solutions are mixed or a drug and a drug solution are dissolved, such as growth hormone preparations, it is necessary to perform the mixture after the needle is attached to the instrument. Accordingly, when the administrator forgets about attaching the needle, it is impossible to achieve the mixture, and further the back-flow or leakage of the drug solution, or the cracking or rupture of the glass tube of the drug solution cartridge adversely occurs as described above. Many of the above-mentioned problems frequently occur, particularly when the patient performs the administration by himself/herself.

Further, in the case of the conventional administration instruments for medical use as shown in FIGS. 24 to 27, the risk of accidents may be low when the doctor or the nurse administers the drug solution, but when the patient by himself/herself performs the administration, an operation of removing air from the syringe which is always performed before the administration may be forgotten if he/she does not always keep it in mind. When the air removal is forgotten, the human bodies of some people may be affected seriously, possibly resulting in a hazardous condition to life.

Further, in the conventional administration instrument for medical use as shown in FIG. 26 or 27, the amount of the injection that has been administered can be displayed on the electronic display unit, but the amount of the injection, the date, and the time at the air removal operation that is always performed before the administration are also recorded in the memory 422, whereby the available space of the memory 422 is uselessly reduced. In addition, since the amount of the injection at the air removal operation is also displayed together with the essential injection amount, when the doctor checks the result of the diagnosis and the past administration history of the administrator (patient) to decide the future remedy, there is a risk that the doctor makes a wrong diagnosis. If the doctor makes such a wrong diagnosis, the body of the administration (patient) may be seriously affected, and a hazardous condition to the life may be produced.

The present invention is made to solve the above-mentioned problems of the conventional administration instruments, and has for its object to provide an administration instrument for medical use that can inject a drug solution safely and with great reliability.

More specifically, the present invention is made to solve the problems of the conventional pen-type or mechanical instrument as shown in FIG. 24 or 25, and has for its object to provide an administration instrument for medical use that prevents the needle from being inserted into the skin more than required even when the injection button is pressed at the administration as well as performs the administration in a stable state.

Further, the present invention is made to solve the problems of the conventional pen-type or mechanical instrument as shown in FIG. 24 or 25, and has for its object to provide an administration instrument for medical use with the reliability, which keeps the length of the needle that is inserted into the skin uniform regardless of the type of the needle that is used by the administrator (patient), to provide a stable administration state, thereby minimizing the failure of the injection or the burden of pain resulting from the injection.

Further, the present invention is made to solve the problems of the conventional pen-type instrument as shown in FIG. 24, and has for its object to provide an administration instrument for medical use which prevents leakage or back-flow of the drug solution, or cracking or rupture of the glass tube containing the drug solution, as well as provides high reliability and safety to the user.

Further, the present invention is made to solve the problems of the conventional instruments as shown in FIGS. 24 to 27, and has for its object to provide an administration instrument for medical use which always informs and makes the administrator aware of air removal before the administration so as to prevent the administrator from forgetting the air removal operation that should be performed before the administration, as well as which is safe and easy to use.

Furthermore, the present invention is made to solve the problems of the conventional instrument which is provided with the electronic device as shown in FIG. 26 or 27, and has for its object to provide an administration instrument for medical use which disables to record the amount of the injection administered, the date, and the time at the air removal operation which is performed by the administrator at the administration in the memory 422, thereby keeping a reliable administration history.

SUMMARY OF THE INVENTION

To attain the above-mentioned object, according to the first aspect of the present invention, there is provided an administration instrument for medical use including: an injection button for administering an injection, which is depressed by an administrator of the injection; and a depressing force transmission unit for transmitting an injection button depressing force to a plunger of a drug solution cartridge that contains the injection at an angle that is not parallel to a longitudinal direction of a needle, thereby enabling administration of the injection by pressing the injection button at an angle that is not parallel to a direction of insertion of the needle.

Therefore, a force that is applied when the injection button is pressed is not transmitted in such a manner as to insert the needle into the skin deeper than the initial insertion of the needle into the skin, thereby not increasing physical and mental pains of the administering patient.

According to the second aspect of the present invention, in the administration instrument for medical use of the first aspect, the depressing force transmission unit includes: a rack which extends in the same direction as that of the depression of the injection button; a first gear which engages with teeth formed on one side of the rack in a longitudinal direction; a second gear which engages with the first gear; and a movable piece which has teeth engaging with the second gear on one side thereof in a direction perpendicular to the rack extending direction, and the movable piece presses the plunger of the drug solution cartridge due to the pressing operation of the injection button.

Therefore, a force that is applied when the injection button is pushed is not transmitted in such a manner as to insert the needle into the skin deeper than the initial insertion of the needle to the skin, thereby not increasing the physical and mental pains of the administering patient.

According to the third aspect of the present invention, the administration instrument for medical use of the first aspect includes: an injection amount setting unit for setting an amount of the injection to be administered.

Therefore, at the administration, only pressing of the injection button is required without looking at a scale that indicates the injection amount, thereby alleviating loads of the administering patient.

According to the fourth aspect of the present invention, in the administration instrument for medical use of the third aspect, the injection amount setting unit includes: a sleeve which is integrated with the plunger, and passes through and engages with the movable piece; and an administration amount adjustment knob which is attached to the sleeve on a side opposite to the plunger, and moves the movable piece within the drug solution cartridge forward or backward by the administrator changing the rotational direction.

Therefore, when the amount of the injection to be administered is previously set by operating the administration amount adjustment knob, only pressing of the injection button is required at the actual administration, without looking at the administration amount scale, thereby alleviating the load of the administering patient.

According to the fifth aspect of the present invention, the administration instrument for medical use of the first aspect includes: an injection button return unit for returning the injection button to its original position when the finger that has pressed the injection button is taken off after the administration.

Therefore, there is no need for the administering patient to return the injection button after the administration to perform the administration again, thereby alleviating the load of the administered patient.

According to the sixth aspect of the present invention, in the administration instrument for medical use of the fifth aspect, the injection button return unit comprises a spring that is sandwiched between an end surface of the rack opposite to the injection button and an inner surface of the administration instrument for medical use.

Therefore, by only adding a simple structure, it is possible to eliminate the need for the administered patient to return the injection button after the administration to perform the administration again, thereby alleviating the load of the administered patient.

According to the seventh aspect of the present invention, in the administration instrument for medical use of the first aspect, a skin touch portion which is touched on the skin at the injection is provided on the same side as a surface of the body of the administration instrument for medical use, on which the needle is located.

Therefore, it is possible to administer the drug solution under a stable state in which the needle does not wobble.

According to the eighth aspect of the present invention, there is provided an administration instrument for medical use including: a skin touch portion that touches the skin of an administrator to stabilize an administration state at administration of a drug solution; a position variable unit for variably changing a position of the skin touch portion; and a skin touch area variable unit for variably changing a skin touch area of the skin touch portion.

Therefore, even when the size of the needle is not uniform and the length of the needle is different depending on the type, it is possible to always make the dimension of the needle that is inserted into the skin constant, thereby eliminating the variations in the amount of the needle that is inserted into the skin. Further, by variably increasing the fixture area of the skin touch portion under the administration state, it is possible to apply the administration instrument for medical use to the skin of the administrator (patient) under a state in which the instrument is held with stability, thereby reducing a failure of the injection or loads of the pain, providing a reliable administration instrument for medical use, and supporting the remedy decided by the doctor with greater reliability.

According to the ninth aspect of the present invention, in the administration instrument for medical use of the eighth aspect, the skin touch position variable unit comprises a mating fixing unit for mating and fixing the skin touch portion to the body of the administration instrument for medical use stepwise at a desired position in a longitudinal direction of a needle.

Therefore, by securely fixing the skin touch position variable unit at a desired position, it is possible to always make the dimension of the needle that is inserted into the skin constant, thereby eliminating the variations in the amount of the needle that is inserted into the skin.

According to the tenth aspect of the present invention, in the administration instrument for medical use of the eighth aspect, the skin touch area variable unit comprises a skin touch width adjustment unit for variably changing an area of a skin touch width by manually sliding a skin touch width adjustment piece including a part of a surface of the skin touch portion.

Therefore, it is possible to easily change/increase the fixture area of the skin touch portion by a manual operation in the administration state, and to apply the administration instrument for medical use to the skin of the administrator (patient) under a stable state where the instrument is held with stability, thereby reducing a failure of the injection or loads of the pain, providing a reliable administration instrument for medical use, and supporting the remedy decided by the doctor with greater reliability.

According to the eleventh aspect of the present invention, there is provided an administration instrument for medical use including: an administration operation inhibit unit for inhibiting an administration operation that is activated by pressing an injection button or an administration button when a needle is not attached to the administration instrument.

Therefore, it is possible to prevent that, when the injection button or the administration button is pressed without the needle being attached to the instrument, the drug solution leaks from the end portion of the instrument opposite to the injection button or the administration button, or the drug solution flows back toward the injection button or the administration button and leaks outside, or the glass tube that contains the drug solution itself is cracked or ruptured and broken due to a pressure that is generated by pressing the injection button or the administration button and accordingly the drug solution in the tube leaks outside.

According to the twelfth aspect of the present invention, in the administration instrument for medical use of the eleventh aspect, the administration operation inhibit unit inhibits an operation of a plunger that forces a drug solution out of the needle when the button operation is performed in a case where the needle is not attached to the administration instrument.

Therefore, when the injection button or the administration button is pressed without the needle being attached to the instrument, it is possible to prevent that the plunger is operated, and accordingly the drug solution leaks from the end portion of the instrument opposite to the injection button or the administration button, the drug solution flows back toward the injection button or the administration button and leaks outside, or the glass tube that contains the drug solution itself is cracked or ruptured and broken due to a pressure that is generated by pressing of the injection button or the administration button and thus the drug solution leaks outside.

According to the thirteenth aspect of the present invention, in the administration instrument for medical use of the eleventh aspect, the administration operation inhibit unit includes: a needle attachment detection unit for detecting whether the needle is attached to the administration instrument or not, whereby it detects that the needle is not attached to the administration instrument, to inhibit the operation of the injection button or the administration button.

Therefore, when the injection button or the administration button is pressed without the needle being attached to the instrument, it is possible to prevent that the drug solution leaks from the end portion of the instrument opposite to the injection button or the administration button, the drug solution flows back toward the injection button or the administration button and leaks outside, or the glass tube that contains the drug solution itself is cracked or ruptured and broken due to a pressure that is generated by pressing of the injection button or the administration button and accordingly the drug solution leaks outside.

According to the fourteenth aspect of the present invention, the administration instrument for medical use of the thirteenth aspect includes: a plunger driving unit for driving the plunger by an operation of the injection button or the administration button, and the needle attachment detection unit engaging with the plunger driving unit when the needle is not attached to the administration instrument to inhibit the operation of the injection button or the administration button.

Therefore, it is possible to detect that the needle is not attached to the administration instrument and to suppress the operation of the injection button or the administration button with a simple structure, whereby when the administrator forgets about attaching the needle to the instrument and presses the injection button or the administration button, it is possible to prevent that the drug solution leaks from the end portion of the instrument opposite to the injection button or the administration button, or the drug solution flow back toward the injection button or the administration button and leaks outside, or the glass tube that contains the drug solution itself is cracked or ruptured and broken due to a pressure that is generated by pressing of the injection button or the administration button and accordingly the drug solution leaks outside.

According to the fifteenth aspect of the present invention, in the administration instrument for medical use of the fourteenth aspect, a resin unit that is integral with the needle contacts the detection unit when the needle is attached to the administration instrument.

Therefore, it is possible to make a compact administration instrument for medical use that can easily detect the presence or absence of the needle.

According to the sixteenth aspect of the present invention, in the administration instrument for medical use of the fifteenth aspect, a resin unit that is integral with the needle is separated from the detection unit when the needle is removed from the administration instrument.

Therefore, it is possible to make a compact administration instrument for medical use with a simple detection mechanism.

According to the seventeenth aspect of the present invention, in the administration instrument for medical use of the fourteenth aspect, the plunger driving unit includes: an injection button for administering an injection, which is depressed by an administrator of the injection; a rack which extends in the same direction as that of the depression of the injection button, and has a cut-away engagement portion in a part; a first gear which engages with teeth formed on one side of the rack in its longitudinal direction; and a second gear which engages with the first gear and teeth that are formed on the plunger in its longitudinal direction, the needle attachment detection unit includes: an eject lever which is located in parallel to the plunger, and has an L-shaped end portion that is sandwiched between the drug solution cartridge and the needle on one end, and a cut-away engagement portion that is formed at a position corresponding to the engagement portion of the rack; and a spring member that pulls the eject lever toward the tip of the needle, and when the needle is not attached to the instrument with the L-shaped end portion being sandwiched, the engagement portions of the eject lever and the plunger engage with each other due to a tension of the spring member, thereby inhibiting the operation of the injection button or the administration button.

Therefore, it is possible to detect that the needle is not attached to the administration instrument to suppress the operation of the injection button or the administration button with a simple structure, whereby it is possible to prevent when the administrator forgets about attaching the needle to the instrument and presses the injection button or the administration button, that the drug solution leaks from the end portion of the instrument opposite to the injection button or the administration button, or the drug solution flows back toward the injection button or the administration button and leaks outside, or the glass tube that contains the drug solution itself is cracked or ruptured and broken due to a pressure that is generated by pressing of the injection button or the administration button and accordingly the drug solution leaks outside.

According to the eighteenth aspect of the present invention, there is provided an administration instrument for medical use that is constructed in such a manner that, when a drug solution cartridge is to be placed in the administration instrument body, the drug solution cartridge cannot be housed normally in the administration instrument body without a needle being attached thereto.

Therefore, it is possible to prevent, when the administrator forgets about attaching the needle to the instrument and presses the injection button or the administration button, that the drug solution leaks from the end portion of the instrument opposite to the injection button or the administration button, or the drug solution flows back toward the injection button or the administration button and leaks outside, or the glass tube that contains the drug solution itself is cracked or ruptured and broken due to a pressure that is generated by pressing the injection button or the administration button and accordingly the drug solution leaks outside.

According to the nineteenth aspect of the present invention, in the administration instrument for medical use of the eighteenth aspect, plural drug solutions are mixed or a drug and a drug solution are dissolved and mixed, and the mixture cannot be performed in the administration instrument body unless a needle is attached thereto.

Therefore, when the needle is not attached to the administration instrument body, the drug solution cartridge cannot be housed in the administration instrument body and accordingly the drug solutions cannot be mixed, whereby it is possible to prevent leakage or flow-back of the drug solution, or cracking or rupture of the glass tube that contains the drug solution.

According to the twentieth aspect of the present invention, in the administration instrument for medical use of the nineteenth aspect, when the drug solution cartridge is to be placed in the body of the administration instrument, a rear rubber part of the drug solution cartridge cannot slide within the drug solution cartridge with contacting a part of the administration instrument, unless a needle is attached to the instrument.

Therefore, when the needle is not attached to the administration instrument body, the drug solution cartridge cannot be housed in the administration instrument body and accordingly the drug solutions cannot be mixed, whereby it is possible to prevent leakage or flow-back of the drug solution, or cracking or rupture of the glass tube that contains the drug solution.

According to the twenty-first aspect of the present invention, in the administration instrument for medical use of the nineteenth aspect, in the drug solution cartridge, different drugs or drug solutions are loaded in a front half of the cartridge to which the needle is attached and a rear opposite half of the cartridge, respectively, the front half of the cartridge has a larger diameter part, the inner diameter of which is larger than the inner diameter of the remaining parts, the rear rubber part is provided on an end surface that is opposite to an end surface of the drug solution cartridge to which the needle is attached, and by depressing the rear rubber part into the drug solution cartridge, a separation rubber that partitions the front half and the rear half of the cartridge is moved to the larger diameter part, thereby mixing the drugs or drug solutions.

Therefore, when the needle is not attached to the instrument, the rear rubber portion of the drug solution cartridge cannot slide within the drug solution cartridge with contacting a part of the administration instrument, and the drug solution cartridge cannot be housed in the administration instrument body when the needle is not attached to the administration instrument and accordingly the drug solutions cannot be mixed, whereby it is possible to prevent leakage or back-flow of drug solution, or cracking or rupture of the glass tube that contains the drug solution.

According to the twenty-second aspect of the present invention, the administration instrument for medical use of the twenty-first aspect includes: a dissolution piece which is fixed to the administration instrument body and pushes the rear rubber part of the drug solution cartridge by sliding the cartridge within the administration instrument body and attaching the same to the body.

Therefore, it is possible to perform mixture of drug solutions within the drug solution cartridge with a simple structure that is added to the administration instrument body.

According to the twenty-third aspect of the present invention, in the administration instrument for medical use of the eighteenth aspect, a retractable door is provided at a position on the administration instrument body in which the drug solution cartridge is loaded when the drug solution cartridge is to be loaded in the administration instrument body.

Therefore, the operation of loading the drug solution cartridge can be easily performed.

According to the twenty-fourth aspect of the present invention, in the administration instrument for medical use of the eighteenth aspect, a needle attachment detection unit for detecting whether the needle is attached to the administration instrument or not is provided between the needle and the administration instrument body.

Therefore, it is possible to make a compact administration instrument for medical use that can easily detect the presence or absence of the needle.

According to the twenty-fifth aspect of the present invention, in the administration instrument for medical use of the twentieth aspect, a sliding piece for sliding the drug solution cartridge and housing the same into the administration instrument body is fixed in synchronization with the needle attachment detection unit which detects that the needle is attached to the drug solution cartridge.

Therefore, by only adding a simple structure, it is possible to house the drug solution cartridge in the administration instrument body smoothly and reliably when the needle is attached, and securely maintain the state of the drug solution cartridge being housed in the instrument.

According to the twenty-sixth aspect of the present invention, in the administration instrument for medical use of the twenty-fifth aspect, the needle attachment detection unit is provided under the sliding piece in parallel to the sliding piece, except for an L-shaped end portion that is sandwiched between the needle and the drug solution cartridge at attachment of the needle, an eject knob is provided which fits into openings that are formed on the sliding piece and the needle attachment detection unit by a depressing urge force, and the openings are formed so that positions of the openings of the sliding piece and the needle attachment detection unit are the same in a state where the needle is not attached yet, while the positions of the openings are different from each other in a state where the needle attachment detection unit is shifted by attaching the needle to the instrument.

Therefore, by only adding a simple structure, it is possible to smoothly and reliably house the drug solution cartridge in the administration instrument body when the needle is attached to the instrument, and securely maintain the state of the cartridge being housed therein.

According to the twenty-seventh aspect of the present invention, there is provided an administration instrument for medical use including an air removal announcement unit for urging an administrator to perform an air removal operation for removing air that remains within a drug solution cabin of the administration instrument before injection.

Therefore, it is possible to make the administrator (patient) aware of air removal and prevent occurrence an accident that the administrator forgets the air removal operation that is to be performed before the administration and then a serious influence is exerted upon the body of the administrator (patient), possibly resulting in a hazardous state for the life, thereby providing a safe and easy-to-use administration instrument for medical use.

According to the twenty-eighth aspect of the present invention, in the administration instrument for medical use of the twenty-seventh aspect, the air removal announcement unit displays a text, a symbol, or a figure, which urges the administrator to perform the air removal operation, as well as outputs voices which urge the administrator to perform the air removal operation.

Therefore, it is possible to display a text, a symbol, or a figure that urges an air removal operation to make the administrator (patient) aware of the air removal, and prevent occurrence of an accident that the administrator forgets about the air removal operation that is to be performed before the administration, and accordingly a serious influence is exerted upon the body of the administrator (patient), possibly resulting in a hazardous state for the life, thereby providing a safe and easy-to-use administration instrument for medical use.

According to the twenty-ninth aspect of the present invention, in the administration instrument for medical use of the twenty-seventh aspect, the air removal announcement unit includes: a first switch for detecting removal of a body cap that is attached over the body of the administration instrument for medical use to which a needle is attached; a air removal display signal generation unit for generating a display signal for the text, the symbol, or the figure that urges the administrator to perform the air removal operation when the first switch detects that the body cap is removed; and a display unit for displaying the display signal for the text, the symbol, or the figure that urges the air removal operation, thereby displaying the text, the symbol, or the figure that urges the administrator to perform the air removal operation when the body cap attached over the body of the administration instrument for medical use to which the needle is attached is removed.

Therefore, it is possible to display a text, a symbol, or a figure that urges an air removal operation when the body cap is removed, to make the administrator (patient) aware of the previous air removal and prevent occurrence of an accident that the administrator forgets the air removal operation that is to be performed before the administration and then a serious influence is exerted upon the body of the administrator (patient), possibly resulting in a hazardous state for the life, thereby providing a safe and easy-to-use administration instrument for medical use.

According to the thirtieth aspect of the present invention, in the administration instrument for medical use of the twenty-seventh aspect, the air removal announcement unit includes: a second switch for detecting that the drug solution cartridge has been loaded into the body of the administration instrument for medical use; an air removal display signal generation unit for generating a display signal for a text, a symbol, and a figure that urges the administrator to perform an air removal operation at a time when the second switch detects that the drug solution cartridge has been loaded into the body of the administration instrument for medical use; and a display unit for displaying the display signal for the text, the symbol, and the figure that urges the air removal operation, thereby displaying the text, the symbol, and the figure that urges the administrator to perform the air removal operation when the drug solution cartridge is loaded into the body of the administration instrument for medical use.

Therefore, it is possible to display a text, a symbol, or a figure that urges an air removal operation when the drug cartridge has been loaded, to make the administrator (patient) aware of the previous air removal, and prevent occurrence of an accident that the administrator forgets the air removal operation that is to be performed before the administration and then a serious influence is exerted upon the administrator (patient), possibly resulting in a hazardous state for the life, thereby providing a safe and easy-to-use administration instrument for medical use.

According to the thirty-first aspect of the present invention, in the administration instrument for medical use of the twenty-seventh aspect, the air removal announcement unit includes: a first switch for detecting removal of the body cap which is attached over the body of the administration instrument for medical use to which the needle is attached; an air removal audio signal generation unit for generating an audio signal that urges the administrator to perform an air removal operation when the first switch detects the removal of the body cap; and a speaker for outputting voices in accordance with the audio signal that urges the air removal operation, thereby outputting the voices that urge the administrator to perform the air removal operation when the body cap is removed.

Therefore, it is possible to output voices that urge an air removal operation when the body cap has been removed, to make the administrator (patient) aware of previous air removal and prevent occurrence of an accident that the administrator forgets an air removal operation that is to be performed before the administration and then a serious influence is exerted upon the body of the administrator (patient), possibly resulting in a hazardous state for the life, thereby providing a safe and easy-to-use administration instrument for medical use.

According to the thirty-second aspect of the present invention, in the administration instrument for medical use of the twenty-seventh aspect, the air removal announcement unit includes: a second switch for detecting that the drug solution cartridge has been loaded into the body of the administration instrument for medical use; an air removal audio signal generation unit for generating an audio signal that urges the administrator to perform an air removal operation when the second switch detects that the drug solution cartridge has been loaded in the administration instrument for medical use; and a speaker for outputting voices in accordance with the audio signal that urges the air removal operation, thereby outputting voices that urge the administrator to perform the air removal operation when the drug solution cartridge has been loaded in the body of the administration instrument for medical use.

Therefore, it is possible to output voices that urge an air removal operation when the drug solution cartridge has been loaded into the instrument, to make the administrator (patient) aware of the previous air removal, and prevent occurrence of an accident that the administrator forgets an air removal operation that is to be performed before the administration, and then a serious influence is exerted upon the body of the administrator (patient), possibly resulting in a hazardous state for the life, thereby providing a safe and easy-to-use administration instrument for medical use.

According to the thirty-third aspect of the present invention, there is provided an administration instrument for medical use including: a needle contact detection unit for detecting that a needle is touching the skin; an injection completion detection unit for detecting that injection has been completed; an injection amount detection unit for detecting an amount of the injection administered; an injection amount recording unit for recording the amount of the injection administered; and a control unit for controlling the injection amount detection unit and the injection amount recording unit to record the amount of the injection administered only when the injection completion detection unit detects that the injection has been completed and the needle contact detection unit detects that the needle is touching the skin.

Therefore, it is possible to detect that the injection has been completed and, at the same time, record the detected amount of the injection only when the needle is touching the skin, to keep only the history at the actual administration with reliability, without keeping the history at the air removal, thereby solving various problems such that the amount of the injection at the air removal operation which is always performed before the administration is also recorded in the memory, and thus the available space of the memory unit is uselessly reduced, or the doctor erroneously judges that administration has been performed though it is not actually performed, in checking the result of the diagnosis and the past administration history of the administrator (patient) and deciding the future remedy, and accordingly a serious influence is exerted upon the body of the administrator (patient), which could result in a state hazardous to the life, whereby it is possible to provide an administration instrument for medical use that can support the remedy decided by the doctor with greater reliability.

According to the thirty-fourth aspect of the present invention, the administration instrument for medical use of the thirty-third aspect includes: a calendar unit for generating a present date information; a clock unit for generating a present time information; and the control unit detecting that the injection has been completed and, at the same time, recording the date and the time of the completion of the injection.

Therefore, it is possible to detect that the injection has been completed and, at the same time, record the detected injection amount and the date and time of the injection only when the needle is touching the skin, to securely keep only the history at the actual administration without keeping the history at the air removal, thereby preventing various problems such that the amount of the injection and the date and time at the air removal operation, which is always performed before the administration, are also recorded in the memory, and thus the available space of the memory unit is uselessly reduced or the doctor erroneously judges that administration has been performed though it is not actually performed, in checking the result of the diagnosis and the past administration history of the administrator (patient) and deciding the future remedy, and accordingly a serious influence is exerted upon the body of the administrator (patient), which could result in a state hazardous to the life, whereby it is possible to provide an administration instrument for medical use that can support the remedy decided by the doctor with greater reliability.

According to the thirty-fifth aspect the thirty-fifth aspect of the present invention, the administration instrument for medical use of the thirty-third aspect includes: a display unit for displaying an injection amount in setting an amount of the injection to be administered, and an injection amount that is recorded when the injection has been completed.

Therefore, it is possible to detect that the injection has been completed and, at the same time, display the detected amount of the injection only when the needle is touching the needle, to securely keep only the history at the actual administration without keeping the history at the air removal, thereby solving various problems such that also the amount of the injection at the air removal operation that is always performed before the administration is displayed, then the doctor erroneously judges that administration has been performed though it is not actually performed, in checking the result of the diagnosis and the past administration history of the administrator (patient) and deciding the future remedy, and accordingly a serious influence is exerted upon the body of the administrator (patient), which could result in a state hazardous to the life, whereby it is possible to provide an administration instrument for medical use that can support the remedy decided by the doctor with greater reliability.

According to the thirty-sixth aspect of the present invention, in the administration instrument for medical use of the thirty-fifth aspect, the display unit displays the date and the time, in addition to the injection amount that is recorded at the completion of the injection.

Therefore, it is possible to detect that the injection has been completed and, at the same time, display the detected injection amount and the date and time only when the needle is touching the skin, to securely keep only the history at the actual administration without keeping the history at the air removal, thereby solving various problems such that also the amount of the injection and the date and time at the air removal operation that is always performed before the administration are displayed, then the doctor erroneously judges that administration has been performed though it is not actually performed, in checking the result of the diagnosis and the past administration history of the administrator (patient) and deciding the future remedy, and accordingly a serious influence is exerted upon the body of the administrator (patient), which could result in a state hazardous to the life, whereby it is possible to provide an administration instrument for medical use that can support the remedy decided by the doctor with greater reliability.

According to the thirty-seventh aspect of the present invention, in the administration instrument for medical use of the thirty-third aspect, the needle contact detection unit includes: a ring-shaped or a semi-ring-shaped contact detection member that slides along the needle at an instant when the needle is inserted; and a third switch that is operated by the sliding of the contact detection member.

Therefore, it is possible to detect that the needle is contacting the skin with a simple structure.

According to the thirty-eighth aspect of the present invention, in the administration instrument for medical use of the thirty-third aspect, the needle contact detection unit includes: a third switch which is on the same side of the skin touch portion as the needle, and is operated during the administration at an instant when the needle is inserted into the skin.

Therefore, it is possible to detect that the needle is contacting the skin with a simple structure.

BRIEF DESCRIPTION OF THE DRAWINGS

FIG. 16 is a perspective view illustrating an administration instrument for medical use according to a fourth embodiment of the present invention before attaching a needle.

FIG. 17 is a cross-sectional view illustrating a part of the administration instrument for medical use according to the fourth embodiment.

FIG. 18 is a block diagram illustrating the administration instrument for medical use according to the fourth embodiment.

DETAILED DESCRIPTION OF THE INVENTION

Embodiment 1

An administration instrument according to the first embodiment is constructed so that an injection button is pressed in a direction that is different from the direction in which a needle is inserted into the skin, thereby preventing the needle from being inserted deeper at the manipulation of the injection button.

Figure 1:
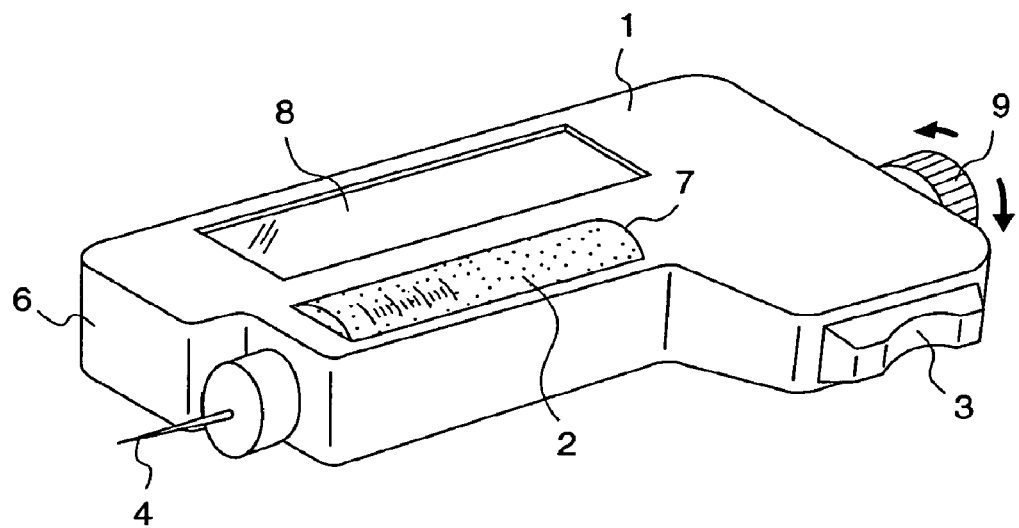
FIG. 1 is a perspective view illustrating an administration instrument for medical use according to a first embodiment of the present invention.
Figure 2:
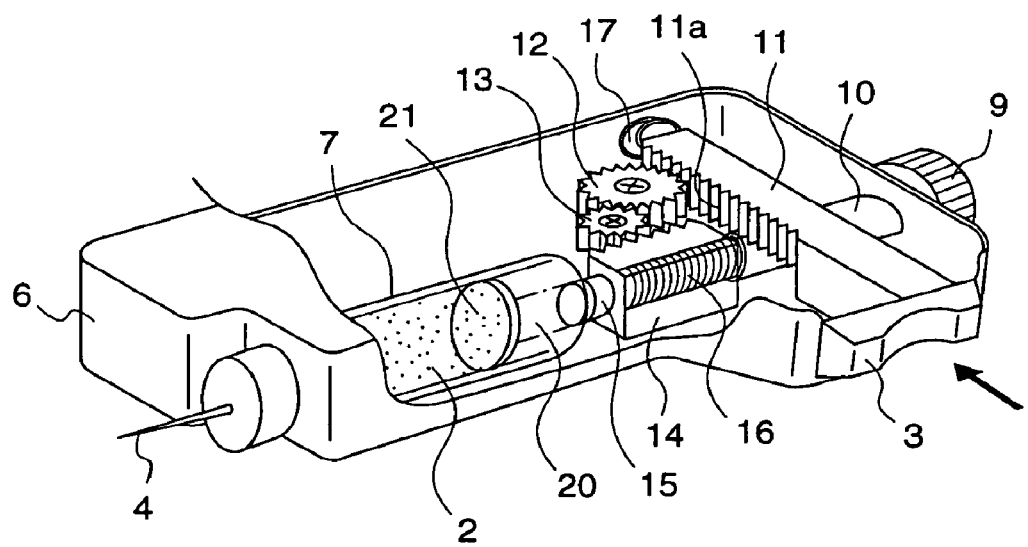
FIG. 2 is a perspective view with portions cutaway of the administration instrument for medical use according to the first embodiment.
Figure 3:
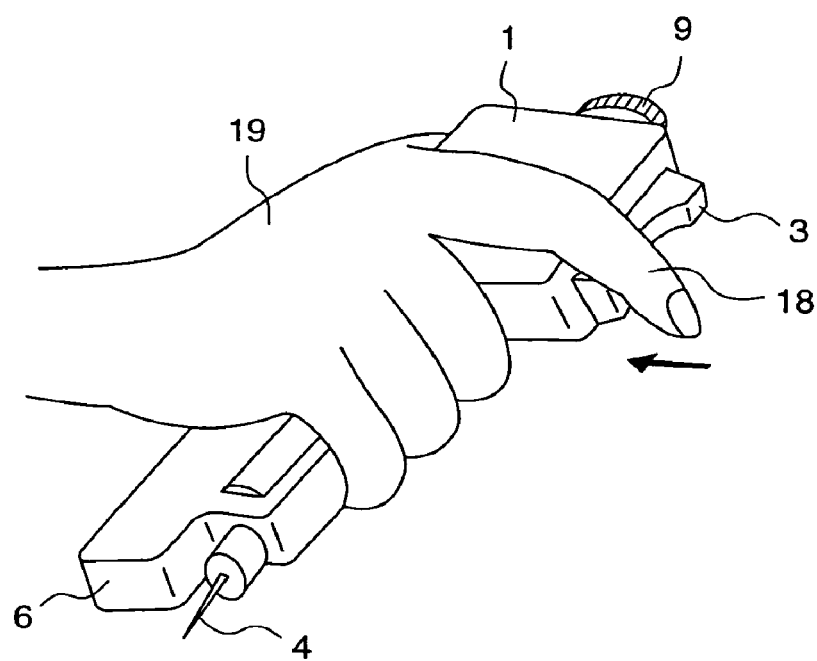
FIG. 3 is a perspective view illustrating a state of the administration instrument for medical use according to the first embodiment, which is actually grasped in a hand.

Hereinafter, the first embodiment will be described with reference to FIGS. 1 to 3. FIG. 1 is a perspective view illustrating an appearance of the administration instrument for medical use according to the first embodiment. FIG. 2 is a perspective view illustrating an internal structure with portion cutaway of the administration instrument for medical use according to the first embodiment. FIG. 3 shows a state where the administration instrument for medical use according to the first embodiment is actually grasped with a hand.

In FIG. 1, reference numeral 1 denotes a body of the administration instrument for medical use, numeral 2 denotes an injection, numeral 3 denotes an injection button, numeral 4 denotes a needle, numeral 6 denotes a skin touch portion, numeral 7 denotes a drug solution cartridge, numeral 8 denotes a liquid crystal display, and numeral 9 denotes an administration amount adjustment knob. Further, the injection button 3 is constructed to be pressed in a direction that is approximately perpendicular to the direction in which the needle 4 is extending. The direction of pressing the injection button 3 may be different from the perpendicular direction so long as it is not parallel to the direction in which the needle 4 is extending, and may form another angle so long as it is in a direction in which the pain of the patient body would be alleviated.

As the procedure of carrying out the injection administration, the drug solution cartridge 7 is initially loaded into the body 1 of the administration instrument for medical use, the needle 4 is attached thereto, and the administration amount adjustment knob 9 is rotated clockwise or counterclockwise as shown by an arrow in the figure, to set the amount of the injection 2 to be administered. Then, the needle is pointed up and the injection button 3 is pressed until the injection 2 flows from the tip of the needle 4, thereby removing air. After completion of this air removal operation, the administration instrument for medical use is grasped in a hand 19 as shown in FIG. 3, then the needle 4 is inserted into the skin with the skin touch portion 6 being touched on the skin where the injection is to be administered, and the administration is performed with pressing the injection button 3 by a forefinger 18 in a direction shown by the arrow in FIG. 3.

Next, descriptions are given of an injection amount setting method and a mechanism in which the injection 2 flows out of the needle 4 when the injection button 3 is pressed, with reference to FIG. 2.

Initially, the injection amount setting method will be described. The administration amount adjustment knob 9 and the sleeve 10 are fixed in the rotational direction, but not fixed in the sliding direction. Further, the sleeve 10 and the plunger 15 that passes through a movable piece 14 are formed integrally. An internal thread 16 is cut inside the movable piece 14 to be engaged with the sleeve 10 within the movable piece 14. An external thread 16 is cut on a part of the sleeve 10 that is included in the movable piece 14 to be engaged within the movable piece 14.

In addition, the plunger 15 is formed by a member that is different from the plunger 20 within the drug solution cartridge 7, and is spaced apart from the plunger 20. At the front end of the plunger 20, a plunger 21 is provided which is made of rubber so as to enable the injection 2 to be forced out of the drug solution cartridge 7 and is fixed to the plunger 20. Further, the amount of sliding of the movable piece 14 is always made constant by the control of a spring 17.

When the administration amount adjustment knob 9 is rotated in a direction of increasing the administration amount, the plunger 15 protrudes through the movable piece 14 further toward the needle. Thus, a space between the plunger 15 and a plunger 20 that is different from the plunger 15 is reduced. The plunger 20 does not move unless it is pushed by the plunger 15. Since the amount of slide of the movable piece 14 in the case of pressing the injection button 3 is always constant, the distance by which the plunger 15 pushes the plunger 20 decides the amount of the injection administered. That is, the stroke of the injection button at the administration is always constant regardless of the amount of the injection to be administered, and thus the administration amount is decided by the amount of slide (protruding allowance) of the plunger 15 from the movable piece 14.

Next, a description will be given of the mechanism of the injection 2 coming out from the needle 4 when the injection button 3 is pushed. In FIG. 2, when the injection button 3 is pushed in the direction of an arrow, a rack 11 that is formed integrally with the injection button 3 also slides in the direction of the arrow. On an end surface of the rack 11 opposite to the injection button 3, a spring (injection button return section) 17 is provided in a form of being compressed when the injection button 3 is pressed and being returned when the pressing of the injection button 3 is stopped due to the resilience. Thus, when the pressing of the injection button 3 is stopped, the injection button 3 returns to the original position due to the returning force of the spring 17.

Teeth 11a are provided on a side of the rack 11, and a gear (first gear) 12 is provided to engage with the teeth 11a, and further a gear 13 (second gear) is provided to engage with the gear 12. Further, teeth are provided on one side of the movable piece 14 to engage with the gear 13. The rack 11, the gear 12, and the gear 13 constitute a depressing force transmitting part that transmits the depressing force of the injection button 3 to the plunger 15 at an angle that is different from the direction in which the needle 4 is extending.

When the injection button 3 is pressed, the rack 11 slides, the gear 12 rotates in a counterclockwise direction, and the gear 13 rotates in a clockwise direction. Then, the movable piece 14 slides together with the plunger 15 in a direction of pushing the plunger 20 and the plunger 21. Then, the plunger 21 slides in a direction of compressing the injection 2 in the drug solution cartridge 7, and then the compressed injection 2 is pushed out from the tip of the needle 4.

The administration instrument for medical use according to the first embodiment transmits the force that is generated when the injection button 3 is pressed by the forefinger 18 in the direction of the arrow in FIG. 3 so as not to insert the needle 4 into the skin deeper than the time when the need is initially inserted into the skin.

Thus, according to the first embodiment, it is possible to prevent the force of pressing the injection button at the administration of the drug solution from being transmitted in a direction of inserting the needle into the skin deeper than the initial insertion of the needle, thereby realizing an administration of the drug solution under a stable condition.

Embodiment 2

In this second embodiment, it is possible to slide the skin touch portion that touches the skin of the administrator at the administration of the drug solution, in a longitudinal direction of the needle and then fix the same, thereby keeping the amount of the tip of the needle that is inserted into the skin constant regardless of the type or size of the needle and alleviating the pain at the administration of the drug solution.

Figure 4:
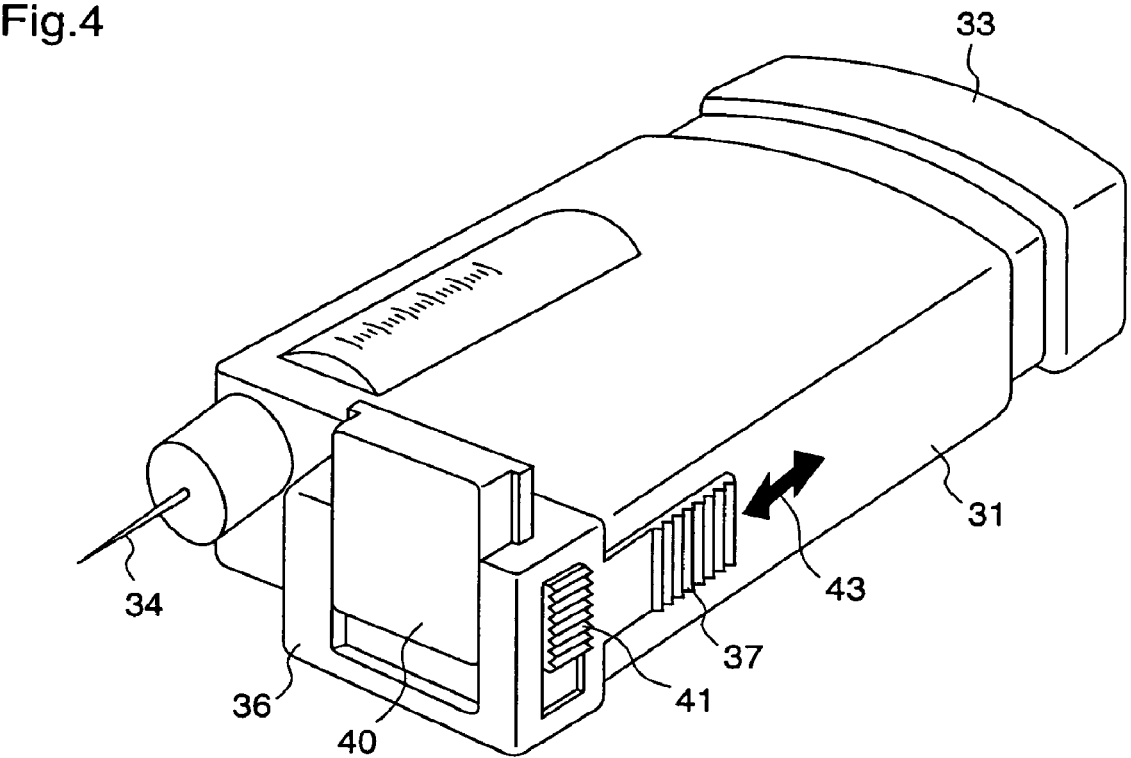
FIG. 4 is a perspective view illustrating an administration instrument for medical use according to a second embodiment of the present invention.
Figure 5:
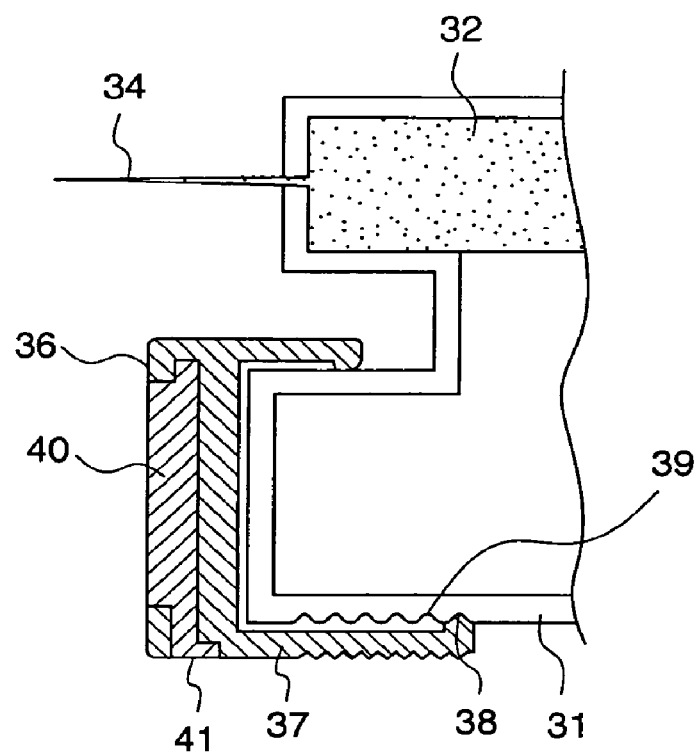
FIG. 5 is a cross-sectional view illustrating a part of the administration instrument for medical use according to the second embodiment.
Figure 6:
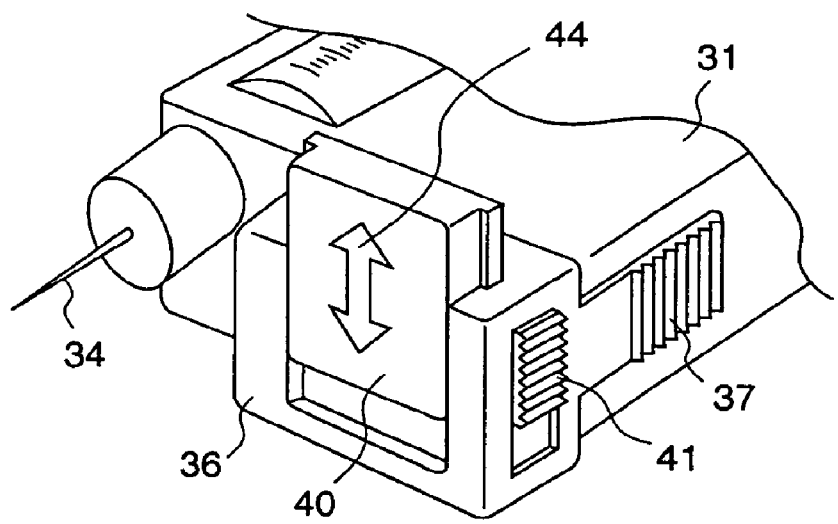
FIG. 6 is a perspective detail view illustrating the administration instrument for medical use according to the second embodiment.
Figure 7:
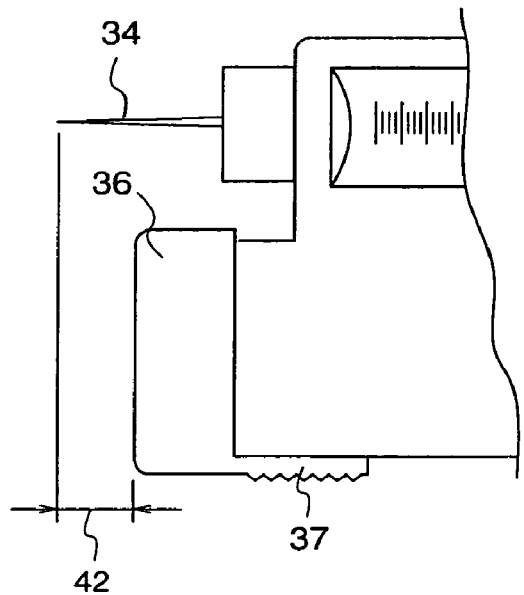
FIG. 7 is a detailed view illustrating a dimension relationship between a needle and a skin touch portion of the administration instrument for medical use according to the present invention.

Hereinafter, the second embodiment will be described with reference to FIGS. 4 to 7. FIG. 4 is a perspective view illustrating an appearance of an administration instrument for medical use according to the second embodiment. FIG. 5 is a cross-sectional view illustrating apart of the administration instrument for medical use according to the second embodiment. FIG. 6 is a perspective detail view illustrating the administration instrument for medical use according to the second embodiment. FIG. 7 is a detailed view showing a relationship between the needle and the skin touch portion of the administration instrument for medical use according to the second embodiment.

In FIG. 4, reference numeral 31 denotes a body of the administration instrument for medical use, numeral 32 denotes an injection, numeral 33 denotes an injection button, numeral 34 denotes a needle, numeral 36 denotes a skin touch portion that is touched on the skin, numeral 37 denotes a skin touch portion adjustment button, numeral 40 denotes a skin touch width adjustment piece (skin touch area variable portion, skin touch width adjustment portion), and numeral 41 denotes a skin touch width adjustment button. The skin touch portion adjustment button 37 is formed integrally with the skin touch portion 36, and can be slid in both directions shown by an arrow 43.

In FIG. 5, the skin touch portion 36 is integral with the skin touch portion adjustment button (skin touch position variable portion) 37, and the skin touch portion adjustment button 37 has dowels (convex portions) 38 and a side surface of the body 31 of the administration instrument for medical use has concave portions 39, as mating fixing parts, so that the skin touch portion 36 and the skin touch portion adjustment button 37 can be stopped and fixed at a desired position.

Therefore, as shown in FIG. 4, it is possible to change the position of the skin touch portion 36 and the skin touch portion adjustment button 37 at a position of a desired concave portion in the direction of the arrow 43 with respect to the needle 34 and fix the same, thereby achieving a desired dimensional relationship 42 between the needle 34 and the skin touch portion 36 as shown in FIG. 7.

Further, in a case of using the same type of the needle 34 at every administration, by adjusting the dimensional relationship 42 of the skin touch portion 36 with respect to the needle 34 to its optimal position and then fixing the same, it is possible to perform the administration every time under the same condition, and make the length of the needle 34 that is inserted into the skin of the administrator (patient) constant, thereby realizing a highly-reliable administration.

In FIG. 6, the skin touch width adjustment piece 40 is integral with the skin touch width adjustment button 41, and is slid in the directions shown by the arrow 44, i.e., in a downward direction in the figure to enlarge the skin touch portion 36, whereby when the administrator touches the skin touch portion 36 on the skin, it is possible to perform an administration under a state where the instrument is held tightly with great stability.

Thus, according to the second embodiment, it is possible to make the length of the needle that is inserted into the skin constant regardless of the type or size of the needle, change the position of the skin touch portion, and further variably increase the skin touch area, whereby the amount of the needle that is inserted into the skin does not vary even when the length of the needle is different depending on the type of the needle, and thus the administration state is stabilized, resulting in a reliable administration instrument for medical use.

It is also possible that the position of the skin touch portion 36 is adjusted steplessly by enabling the skin touch portion 36 to be fixed at an arbitrary position, in place of the dowels and the concave portions.

Further, it is also possible to alleviate the pain at the injection by constructing the internal structure in the same manner as the first embodiment, and making the direction of the pressing of the injection button different from the direction in which the needle 204 is inserted into the skin.

Embodiment 3

This embodiment inhibits pressing of the injection button or the administration button when the needle is not attached to the instrument body, and further, also in the case of mixture-type drug solution administration, prevents the drug solutions from being mixed and housed within the instrument body when the needle is not attached to the instrument body, thereby preventing a leakage or back-flow of the drug solution, or cracking or rupture of the glass tube that contains the drug solution.

Figure 8:
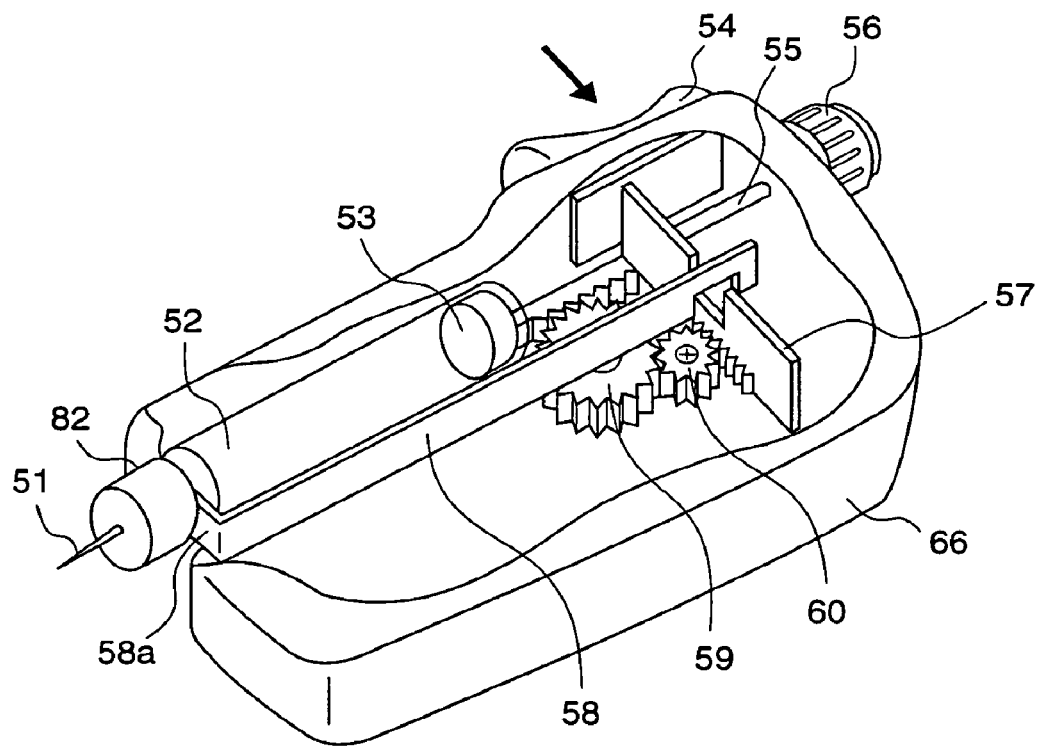
FIG. 8 is a perspective view for explaining an internal structure of an administration instrument for medical use according to a third embodiment of the present invention with portions cutaway.
Figure 9:
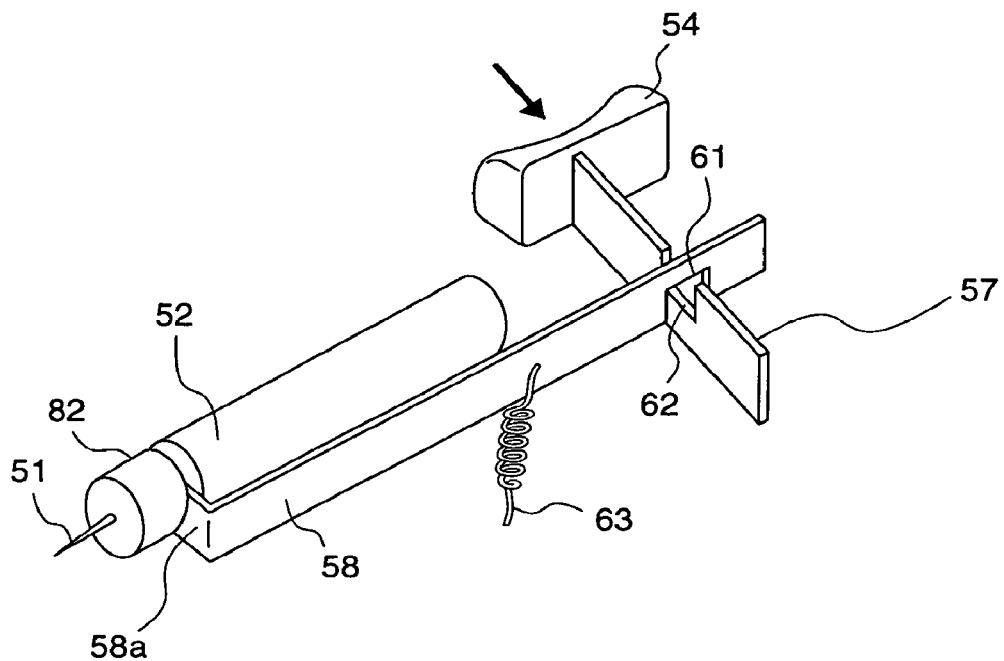
FIG. 9 is a perspective view illustrating a positional relationship between an administration button (or an injection button) and an eject lever, for explaining an operation principle of the administration instrument for medical use according to the third embodiment.
Figure 10:
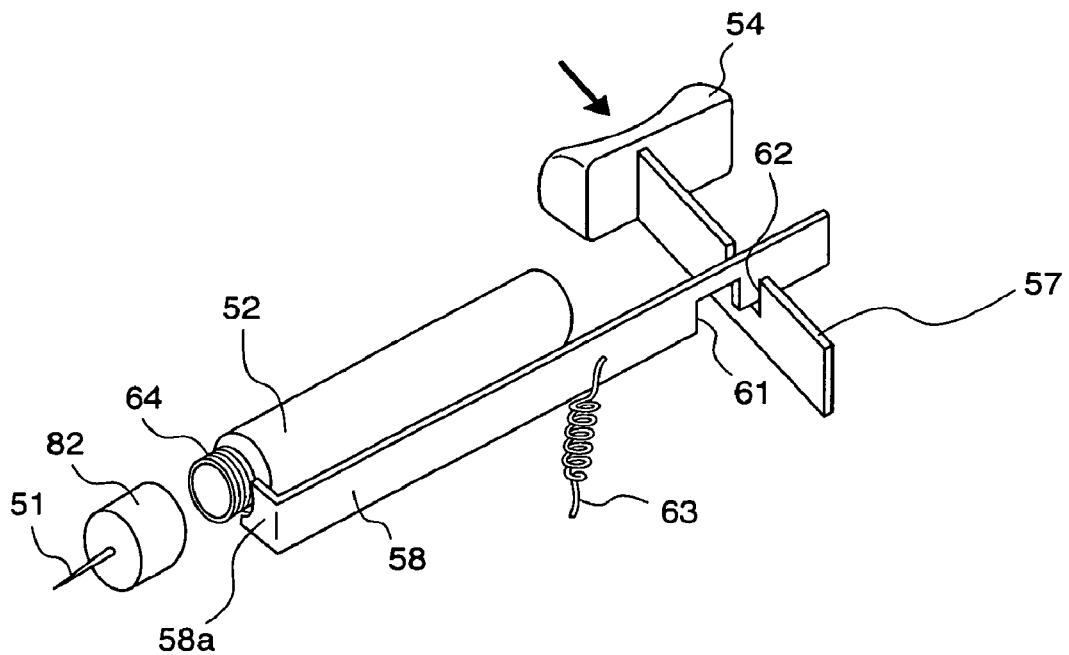
FIG. 10 is a perspective view illustrating a positional relationship between an administration button (or an injection button) and an eject lever, for explaining the operation principle of the administration instrument for medical use according to the third embodiment.
Figure 11:
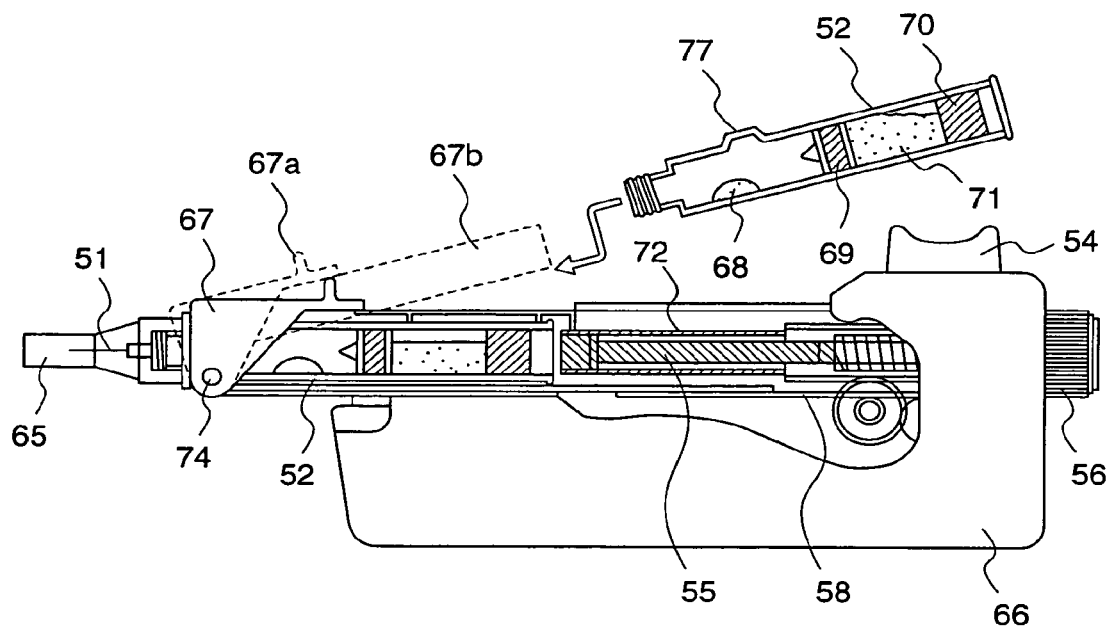
FIG. 11 is a view illustrating a drug solution cartridge mounting state of the administration instrument for medical use according to the third embodiment partially in cross section.
Figure 12:
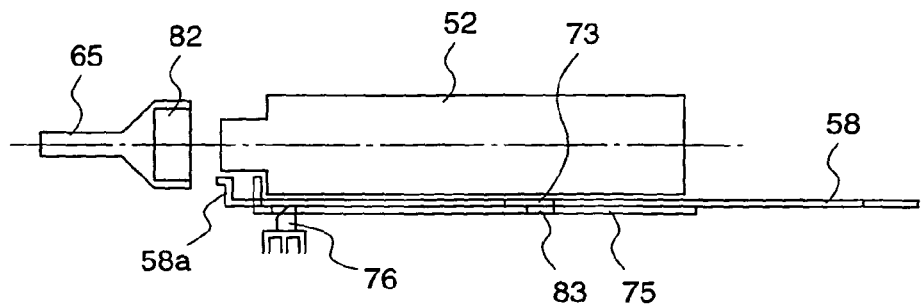
FIG. 12 are diagrams showing positional relationships between a detection mechanism and an injection button of the administration instrument for medical use according to the third embodiment when a needle is not attached thereto.
Figure 12:
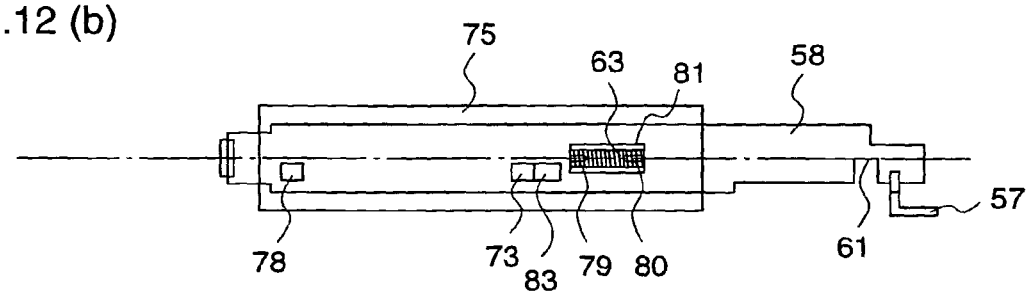
Figure 13:
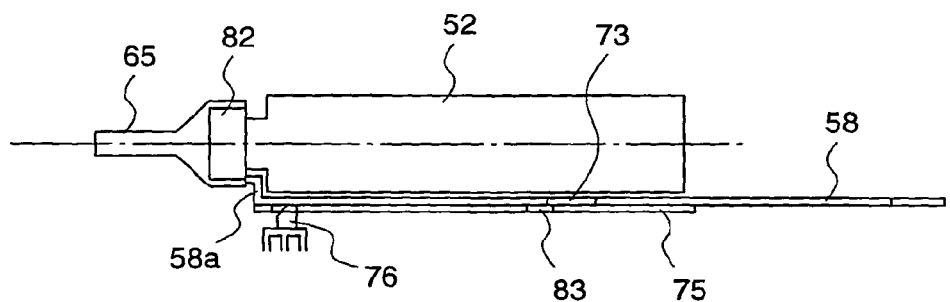
FIG. 13 are diagrams showing positional relationships between a detection mechanism and an injection button of the administration instrument for medical use according to the third embodiment when a needle is attached thereto.
Figure 13:
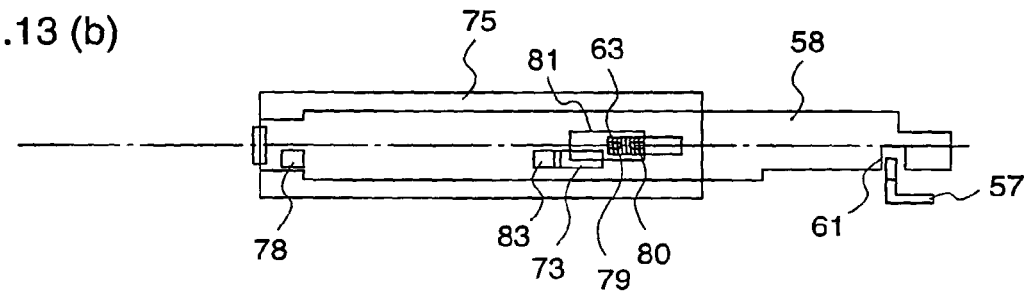
Figure 14:
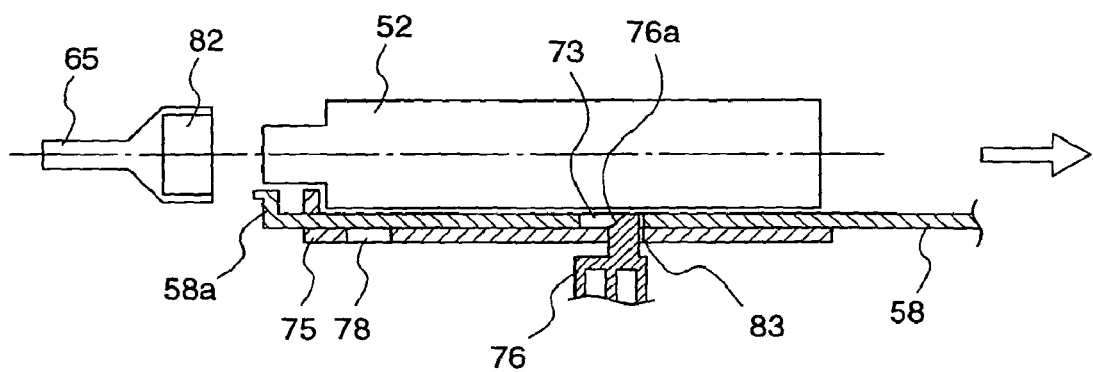
FIG. 14 is a positional relationship between a detection mechanism and a fix/release mechanism of the administration instrument for medical use according to the third embodiment when a needle is not attached thereto.
Figure 15:
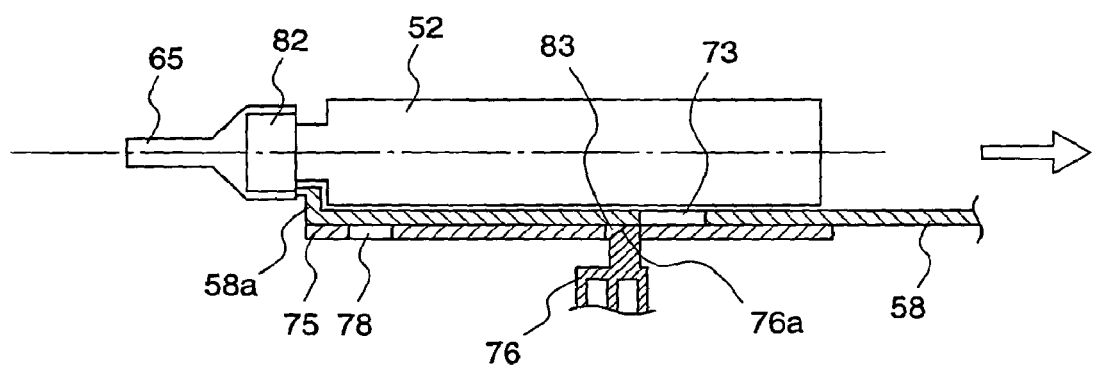
FIG. 15 is a positional relationship between a detection mechanism and a fix/release mechanism of the administration instrument for medical use according to the third embodiment when a needle is attached thereto.

Hereinafter, the third embodiment of the present invention will be described with reference to FIGS. 8 to 15. FIG. 8 is a perspective view illustrating an internal structure with portions cutaway of the administration instrument for medical use according to the third embodiment. FIG. 9 is a perspective view for intelligibly explaining the operation principle of the administration instrument for medical use according to the third embodiment when the needle is attached thereto. FIG. 10 is a perspective view for intelligibly explaining the operation principle of the instrument when the needle is not attached thereto. FIG. 11 is a cross-sectional view with portions cutaway of the administration instrument for medical use according to the third embodiment, for explaining an operation of attaching a drug solution cartridge. FIG. 12 are diagrams showing positional relationships between a detection mechanism and an injection button of the administration instrument according to the third embodiment when the needle is not attached thereto. FIG. 13 are diagrams showing positional relationships between the detection mechanism and the injection button of the administration instrument according to the third embodiment when the needle is attached thereto. FIG. 14 is a diagram showing a positional relationship between a detection mechanism and a fix/release mechanism of the administration instrument for medical use according to the third embodiment when the needle is not attached thereto. FIG. 15 is a diagram showing a positional relationship between the detection mechanism and the fix/release mechanism of the administration instrument for medical use according to the third embodiment when the needle is attached thereto.

In FIG. 8, the mechanism of injecting is briefly described. A drug solution cartridge 52 is placed in the body of an administration instrument 66, and a disposable needle 51 is attached to the drug solution cartridge 52. When the drug solution is administered to a human body, an administration amount setting knob 56 is adjusted to an amount to be administered. Since a plunger 55 is fixed to the administration amount setting knob 56 in the rotation direction but not fixed in the sliding direction, the plunger is expandable or contractible in a direction parallel to the needle when the administration amount setting knob 56 is rotated. When the administration amount is set in the direction of increasing the amount, the plunger 55 is moved in the same direction as the needle toward the tip.

When an administration button 54 is depressed, an injection button-integrated driving lever 57 is moved in the same direction as the depressing of the injection button. A part of a side of the injection button-integrated driving lever (injection button, rack) 57 has a gear (rack) that engages with a gear (first gear) 60. Further, a gear (second gear) 59 engages with the gear 60 and a gear (rack) at the end portion of the plunger 55. At the end of the plunger 55, a drug solution pushing plunger 53 is provided, which contacts with the drug solution within the drug solution cartridge 52. The injection button-integrated driving level 57, the gear 60, and the gear 59 constitute a driving unit of the plunger 55.

When the injection button 54 is pressed in a direction as shown by an arrow of FIG. 8, the injection button-integrated driving lever 57 rotates the gear 60 in a clockwise direction. By the rotation of the gear 60, the gear 59 is rotated in a counterclockwise direction while moving the plunger 55 in a longitudinal direction of the needle 51, i.e., moves the plunger 55 toward the left in FIG. 8. Then, the drug solution pushing plunger 53 that is located at the end of the plunger 55 forces the drug solution included in the drug solution cartridge 52 out of the needle 51, thereby achieving the administration.

In FIG. 9, an end portion (L-shaped end portion) 58*a* of an eject lever 58 is sandwiched between a resin part 82 of the needle 51 and the drug solution cartridge 52. At this time, when the injection button 54 is pressed in the direction of the arrow, the injection button-integrated driving lever 57 can freely move within an engagement portion 61 of the eject lever 58. The eject lever 58 and the injection button-integrated driving lever 57 constitute an administration operation suppression unit that suppresses the administration operation that is caused by pressing the injection button. Further, the end portion (detection member) 58*a* of the eject lever 58 is integral with the body of the eject lever 58, and accordingly when the needle 51 that is formed integrally with the resin part 82 is attached to the instrument, a stress is always applied toward the needle 51 due to a spring 63. The spring (spring member) 63 and the eject lever 58 constitute a needle attachment detection part.

When the needle 51 is removed from the drug solution cartridge 52 as shown in FIG. 10, the part of the eject lever 58 moves toward the needle 51, i.e., toward the left in FIG. 9 due to the stress of the spring 63. Then, the engagement portion 61 of the eject lever 58 is disengaged from the engagement portion 62 of the injection button-integrated driving lever 57. When the injection button 54 is pressed in the direction as shown by the arrow at this time, the engagement portion 62 immediately hits the side of the eject lever 58, thereby preventing a free movement. That is, when the needle 51 is removed, it becomes impossible to completely press the injection button 54. As described above, according to the third embodiment, whether the needle is attached to the instrument or not is detected at the end 58*a* of the eject lever 58.

Next, a description will be given of a method of placing the drug solution cartridge 52 in the instrument body 66 to house the same in the instrument body 66, in a case of a drug solution cartridge for dissolving and mixing a drug and a drug solution, with reference to FIG. 11.

In FIG. 11, a drug solution cartridge holding lid (retractable door) 67 is raised up to a state shown by a dashed line in the figure, and the drug solution cartridge 52 is inserted in the direction as shown by an arrow in this figure. After the insertion, the drug solution cartridge holding lid 67 is lowered and closed. Next, the needle 51 is screwed into a top threaded part of the drug solution cartridge 52 with a needle cap 65 being placed over.

Next, a projection 67*a* is held and slid toward the administration amounts setting knob 56. Then, a rear rubber part 70 inside the drug solution cartridge 52 initially hits a dissolving piece 72 in the administration instrument body 66. When the projection is further slid, the dissolving piece 72 will press the rear rubber part 70, whereby a drug solution 71 that is filled in the rear half of the cartridge moves a separation rubber 69 toward the front half of the cartridge, which contains a drug 68.

When the separation rubber 69 is moved up to an injection slot 77, the drug solution 71 passes the injection slot (larger diameter part) 77, and flows into the drug 68. When the projection 67a is held and slid further toward the administration amount setting knob 56, all of the drug solution 71 flows into the cabin of the drug 68 through the injection slot 77, whereby consequently the drug 68 and the drug solution 71 are mixed. When the projection 67a is held and slid further toward the administration amount setting knob 56, it cannot be slid more and is fixed at a time when the rear rubber part 70 hits the separation rubber 69. This fixed structure will be described later with reference to FIG. 15. In this state, the drug solution cartridge 52 is housed within the administration instrument body 66.

Next, relationships between the detection mechanism and the injection button-integrated lever 57 when the needle is attached to the instrument and when the needle is not attached thereto will be shown in FIGS. 12 and 13, respectively, in detail. FIG. 12 show a state where the needle is not attached to the instrument, and FIG. 13 show a state where the needle is attached thereto. Here, the term "needle" in descriptions of FIGS. 12 to 15 refers to the needle 51 that is covered by a cap 65.

In FIG. 12(a), the drug solution cartridge 52 is kept at the end of a sliding lever 75. The eject lever 58 is located over the sliding lever 75, and is capable of freely moving in a direction parallel to the needle attachment direction on the sliding lever 75.

FIG. 12(b) is a diagram illustrating the instrument of FIG. 12(a) when viewed from the bottom. The sliding piece 75 has a slit 78 and a slit 83, which can accommodate an eject knob 76. The eject lever 58 has a slit 73 at a position corresponding to the slit 83.

At the center of the sliding piece 75 and the eject lever 58, slits 81 of the same width are provided at their corresponding positions, respectively. Further, within the slits 81, a spring 63 that can be accommodated within the entire thickness dimension of the sliding piece 75 and the eject lever 58 is provided parallel to the sliding piece 75. Besides, the spring 63 is latched inside the slit 81 and between a projection 79 that projects from the sliding piece 75 and a projection 80 that projects from the eject lever 58. At this time, the engagement portion 61 of the eject lever 58 is in such a positional relationship that the injection button-integrated driving lever 57 cannot freely move within the engagement portion 61. That it, it is in a state where the injection button cannot be pressed.

Next, in FIG. 13, when the needle is attached to the drug solution cartridge 52, the end 58a of the eject lever 58 is pressed up to the end position of the sliding piece 75. Then, the spring 63 within the slit 81 is kept in compression from the state as shown in FIG. 12(b). On the other hand, the engagement portion 61 of the eject lever 58 gets in a positional relationship such that the injection button-integrated lever 57 can freely move. That is, the injection button is capable of being pressed in this state.

Next, descriptions will be given of the principle that the drug solution cartridge 52 cannot be housed within the administration instrument body 66 when the needle is attached to the drug solution cartridge 52 and the cartridge 52 can be housed within the instrument body 66 when the needle is attached to the instrument, with reference to FIGS. 14 and 15.

In FIG. 14, when the needle is not attached to the drug solution cartridge 52, the end portion 58a of the eject lever 58 is protruding beyond the end of the sliding piece 75 toward the needle. At this time, the eject knob 76 that is urged by a spring (not shown) in an upward direction latches the sliding piece 75 so as not to move either toward the needle or in the inverse direction in a state where the knob 76 is passing through two slits, i.e., the slit (opening) 73 on the eject lever 58 and the slit (opening) 83 on the sliding piece 75. Here, the eject knob 76 is placed in a direction perpendicular to the sliding piece 75 and the eject lever 58, and is in a state of constantly being pushed upward by the spring with respect to FIGS. 14 and 15.

In FIG. 15, when the needle is attached to the drug solution cartridge 52, the end portion 58a of the eject lever 58 is shifted to the same position as the end of the sliding piece 75. In the process of screwing (attaching) the needle to the drug solution cartridge 52, the inner surface of the slit 73 on the eject lever 58 pushes a sloped portion 76a of the eject knob 76 in a direction shown by an arrow, and accordingly the eject know 76 is gradually pushed downward. When the needle is further screwed, the slit 73 on the eject lever 58 is moved in a direction of pushing the sloped portion 76a of the eject knob 76 further downward. Then, when the needle is completely attached to the drug solution cartridge 52, the slit 73 of the eject lever 58 has pushed down the end of the eject knob 76 and passed through, and the eject knob 76 is within the slit 83 of the sliding piece 75, thereby latching the sliding piece 75 in a direction opposite to the arrow.

To house the drug solution cartridge 52 in the administration instrument body 66 under this state, the drug solution cartridge 52 that is located on the sliding piece 75 is slid in the direction shown by the arrow together with the sliding piece 75.

Practically, as described with reference to FIG. 11, the drug solution cartridge is moved with being placed within the drug solution cartridge holding lid 67, and only the principle has been given here.

When the drug solution cartridge 52 on the sliding piece 75 is moved together with the sliding piece 75 in the direction shown by the arrow, i.e., toward the right in FIG. 14, the slit 83 hits the sloped portion 76a of the eject knob 76. When the cartridge is further moved from this point in the direction of the arrow, the eject knob 76 is pushed by the sliding piece 75 in a downward direction, and when the sliding piece 75 is moved further in the direction of the arrow, the end portion of the eject knob 76 fits into the slit 78 of the sliding piece 75, and at the same time, latches the sliding piece 75 at that position, thereby preventing the sliding piece from being moved in a direction opposite to the arrow.

This state is shown in FIG. 13(a). To release this state, a slide knob that is integral with the eject knob 76 is provided outside the administration instrument body 66, and this slide knob is forcefully pushed down lightly by a finger, thereby enabling the releasing operation.

When two kinds of drug solutions are mixed in the administration instrument body, or a drug and a drug solution are dissolved and mixed as described with reference to FIG. 11, this instrument inhibits the mixing because the cartridge cannot be placed within the administration instrument body unless the needle is attached thereto.

As described above, according to the third embodiment, the injection button or the administration button cannot be pushed and the plunger that forces the drug solution out of the instrument does not operate when the needle is not attached to the administration instrument, and further in the case of mixture-type drug administration instrument, it is impossible to perform the mixing when the needle is not attached to the administration instrument. Therefore, when the needle is not attached to the administration instrument body, it is impossible to push the injection button or the administration button even if the administrator erroneously intends to push the button, thereby preventing leakage of the drug solution or rupture of the glass tube or the like, which is caused by the erroneous operation.

Embodiment 4

According to this fourth embodiment, an alarm display is performed to alert the administrator to carry out an air removal operation when performing the injection with an administration instrument for medical use including an electronic device.

Hereinafter, the fourth embodiment will be described with reference to FIGS. 16 to 18. FIG. 16 is a perspective view illustrating an appearance of an administration instrument for medical use according to the fourth embodiment before attaching a needle, FIG. 17 is a cross-sectional view illustrating a part of the administration instrument for medical use according to the fourth embodiment, and FIG. 18 is a block diagram showing a microprocessor 25 in the center.

In FIG. 16, numeral 102 denotes a cap for the instrument body, numeral 103 denotes a body of the administration instrument for medical use, numeral 104 denotes a display, numeral 105 denotes an administration amount setting dial, numeral 106 denotes an injection button, and numeral 127 denotes a speaker.

Initially, a description is given of a case where the administration instrument for medical use is first employed. In FIGS. 16 and 17, when the cap 102 for the body is removed from the body 103 of administration instrument for medical use, a switch (first switch) 110 that is provided on the body 103 of the administration instrument for medical use is switched from ON to OFF. At this time, function displays that are displayed on the display 104 are all lighted up and, after several seconds, only the calendar, the time, and the administration amount are displayed.

In FIG. 17, screw parts 109a and 109b of the body 103 of the administration instrument for medical use are engaged by threads, respectively. The screw parts 109a and 109b are rotated in a direction where the threads are loosen, thereby separating the body 103 of the administration instrument for medical use into two screw units 103a and 103b. After the separation, a drug solution cartridge is placed in the screw unit 103a, then the screw units 103a and 103b are engaged again at the screw parts 109a and 109b, and the screw units 103a and 109b are rotated in a direction of being fixed, resulting in the original administration instrument 103 for medical use. Then, a cartridge detecting switch (second switch) 111 that is provided inside the administration instrument 103 for medical use is switched from OFF to ON.

Figure 32:
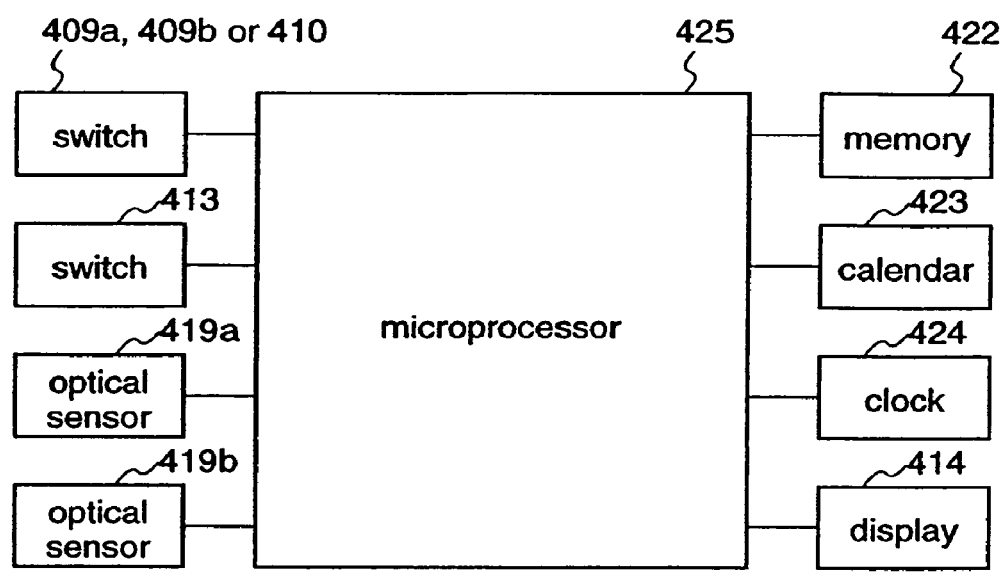
FIG. 32 is a block diagram for explaining the conventional administration instrument for medical use.
Figure 33:
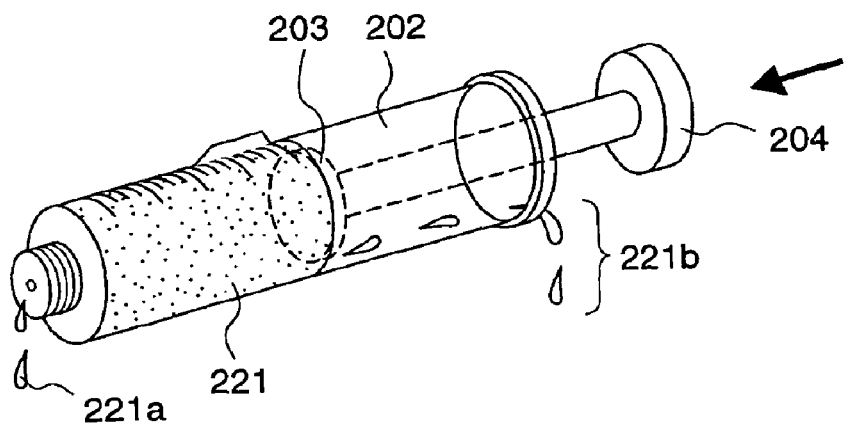
FIG. 33 is a perspective view showing an operating state of the conventional administration instrument for medical use.
Figure 34:
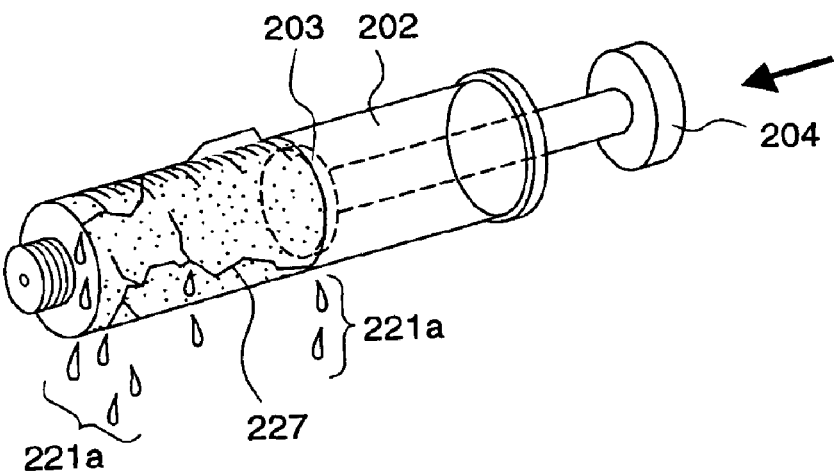
FIG. 34 is a perspective view showing another operating state of the conventional administration instrument for medical use.

When this state has been achieved, a text "Remove air" appears on the display 104, and starts blinking. In synchronization with this blinking, a voice of "Remove air, please" is outputted from the speaker 127. Then, the administrator attaches the needle 101 to the instrument, turns the needle 101 upward, and presses the injection button 106 with the injection button 106 facing downward until the drug solution 126 comes out from the needle 101. Then, as described in the prior art, the switch 113 (corresponding to the switch 413 in FIG. 32 as described as the prior art) is turned ON once and turned OFF again. This state of the switch 113 is employed also to judge completion of the air removal, and the microprocessor (air removal display signal generation unit) 125 judges that the air removal has been completed.

Here, the above-mentioned blinking of the text of "Remove air" and announcement by voices are continued until the microprocessor 125 judges the state of the switch 113 as the completion of the air removal. Further, the judgement of the states of the switches 110 and 111, and a display instruction and a voice announcement instruction for the display 104 are carried out by the microprocessor (air removal audio signal generation unit) 125 of FIG. 18. That is, the microprocessor 125, the display 104, and the speaker 127 constitute an air removal announcement section. Further, in this FIG. 18, reference numeral 123 denotes a calendar for generating date information, and numeral 124 denotes a clock for generating time information.

Next, a description will be given of a state where the drug solution cartridge 107 is already placed in the administration instrument 103 for medical use, i.e. a case of the second or following administration. When the body cap 102 is removed from the administration instrument 103 for medical use, the switch 110 that is provided on the body 103 of the administration instrument for medical use is switched from ON to OFF. At this time, the function displays that are displayed on the display 104 are all lighted up and, after several seconds, only the calendar, the time, and the administration amount are displayed.

Then, the text of "Remove air" is blinked on the display 104 and, in synchronization with this, the voice "Remove air, please" is outputted from the speaker 127. Then, the administrator attaches the needle 101 to the instrument, and presses the injection button 106 with facing the needle 101 upward and the injection button 106 facing downward until the drug solution 126 comes out of the needle 101. Then, as in the case of the first usage, the microprocessor 125 judges that the air removal has been completed from the state of the switch 113, and then the display of the text "Remove air" is turned off, and further the voice announcement "Remove air, please" is stopped.

Here, the means for detecting the completion of the injection, the means for detecting the amount of the injection administered, the means for recording the amount of the injection administered, and the means for detecting the completion of the injection and the amount of the injection administered and simultaneously recording and displaying the detected amount of the administered injection, the date, and the time are the same as those described in the prior art.

The display for urging the administrator to perform the air removal in the above descriptions can be made not only by the text but also using a symbol or a figure. Further, it is also possible to urge the administrator to perform the air removal operation by one of the display and the voices.

As described above, according to the fourth embodiment, the text of "Remove air" is displayed on the display when the body cap that is placed over the needle attachment part of the administration instrument for medical use to which the needle is attached, is removed. Therefore, it is possible to make the administrator of the drug solution aware of the air removal operation before the administration, thereby urging the administrator to perform the "air removal" operation.

Embodiment 5

This embodiment can solve a problem of the administration instrument for medical use having an electronic device, that the amount of an injection that is preliminarily outputted at the air removal is recorded without being distinguished from the essential injection.

Figure 19:
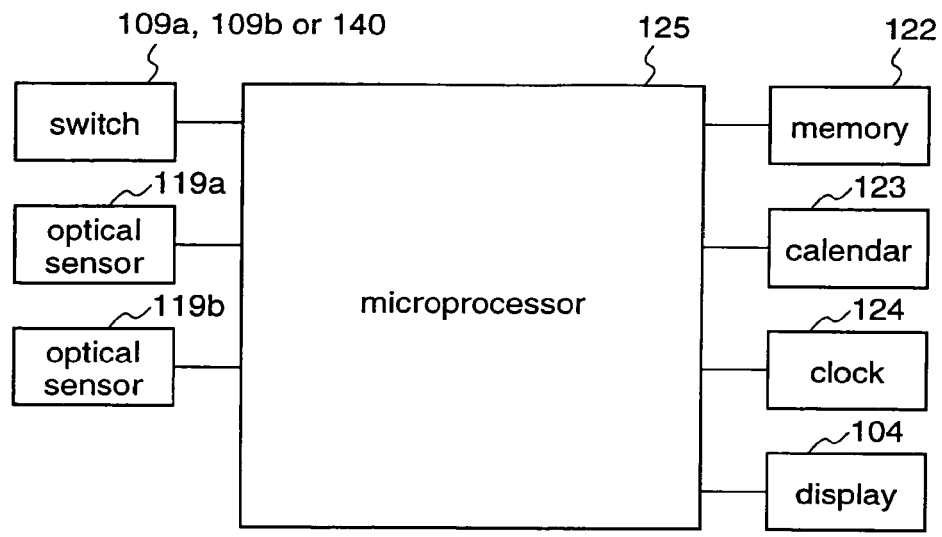
FIG. 19 is a block diagram for explaining the administration instrument for medical use according to the fourth embodiment.
Figure 20:
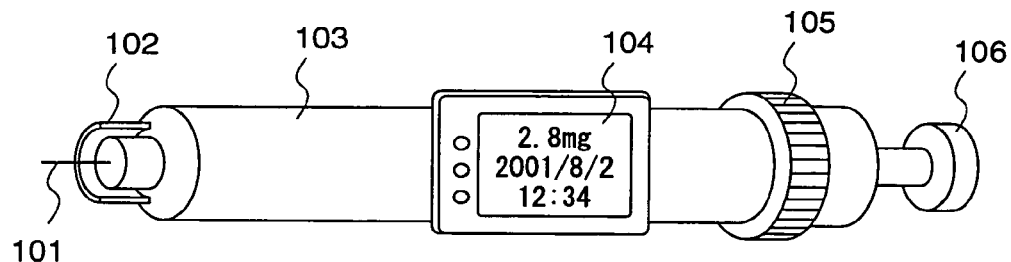
FIG. 20 is a perspective view illustrating an administration instrument for medical use according to a fifth embodiment of the present invention.
Figure 21:
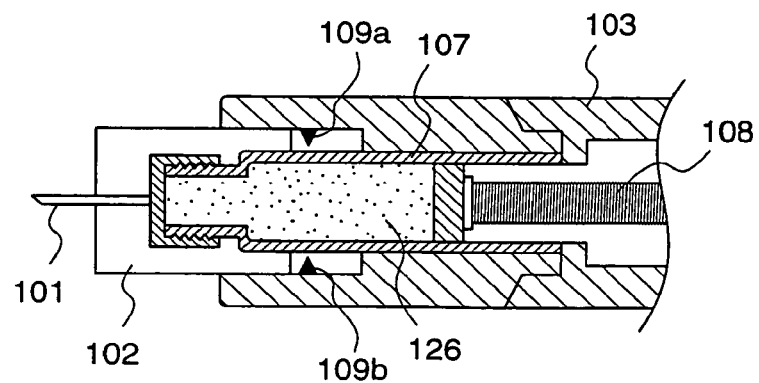
FIG. 21 is a cross-sectional view illustration a part of the administration instrument for medical use according to the fifth embodiment.
Figure 22:
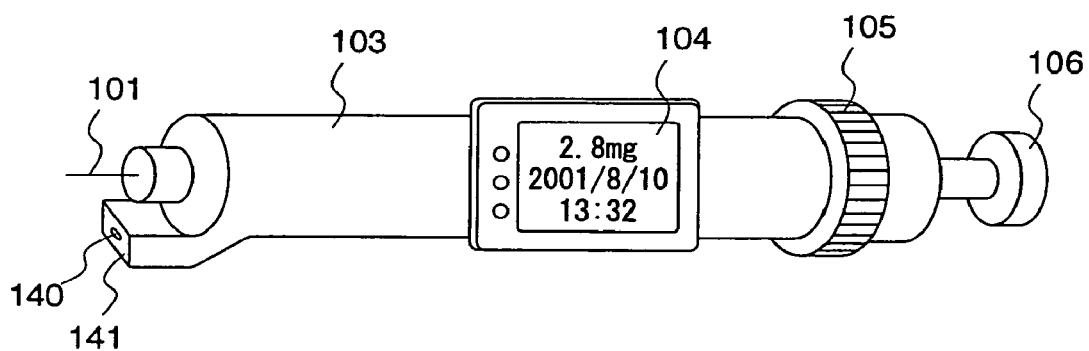
FIG. 22 is a perspective view illustrating a variation of the administration instrument for medical use according to the fifth embodiment.
Figure 23:
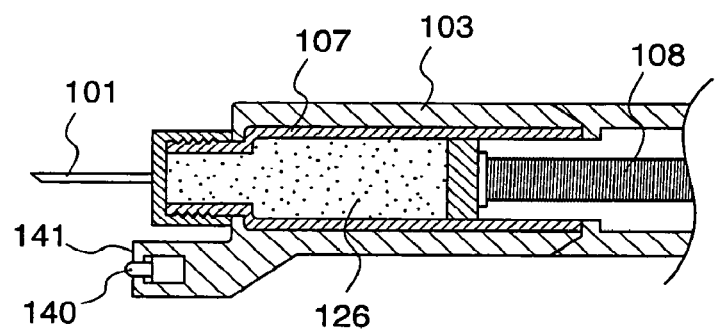
FIG. 23 is a cross-sectional view illustrating a part of the variation of the administration instrument for medical use.
Figure 24:
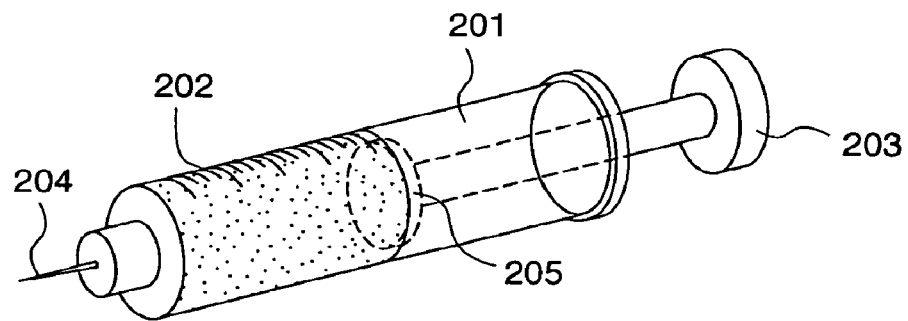
FIG. 24 is a perspective view illustrating a conventional administration instrument for medical use.
Figure 25:
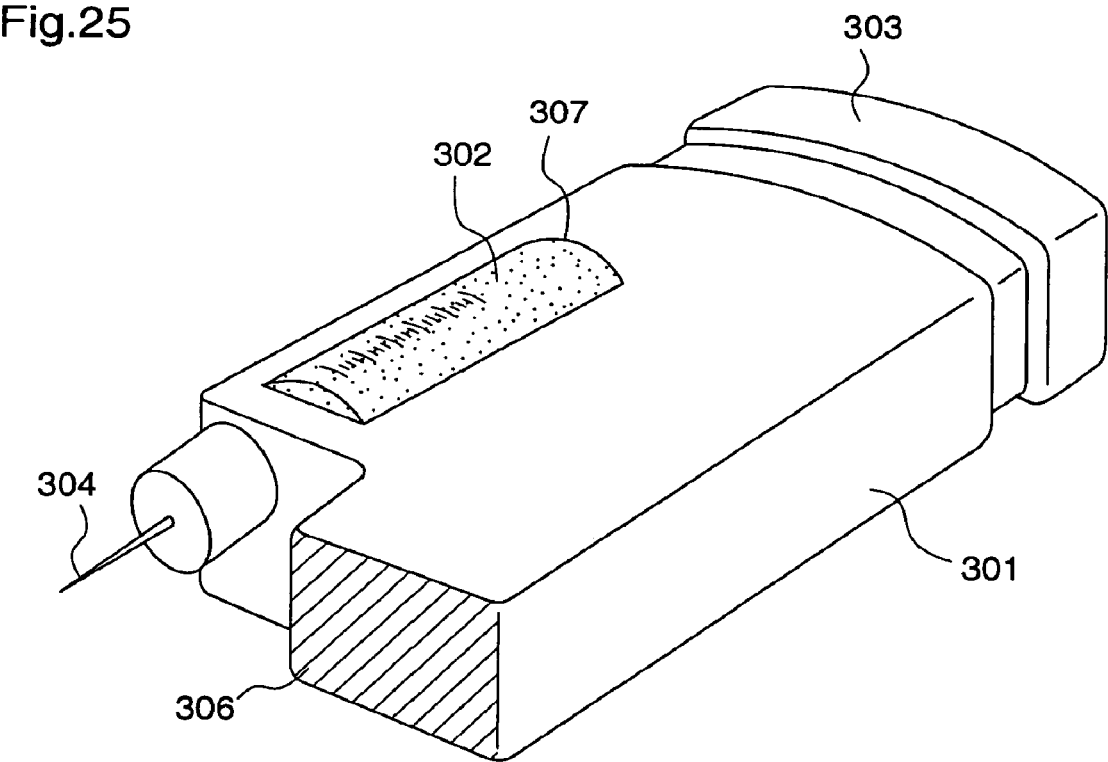
FIG. 25 is a perspective view illustrating another conventional administration instrument for medical use.
Figure 26:
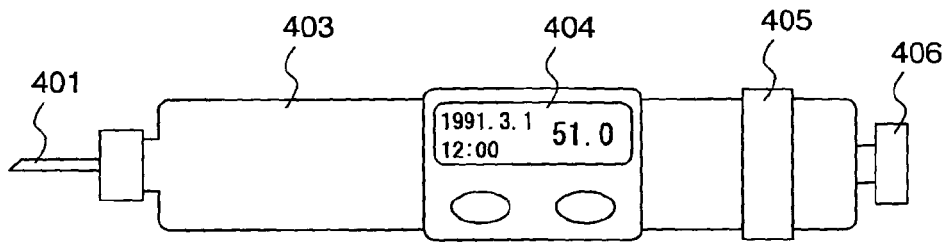
FIG. 26 is a front view illustrating the conventional administration instrument for medical use.

Hereinafter, the fifth embodiment will be described with reference to FIGS. 19 to 23. FIG. 19 is a block diagram illustrating an administration instrument for medical use according to the fifth embodiment with a microprocessor 125 in the center. FIG. 20 is a perspective view illustrating an appearance of the administration instrument for medical use according to the fifth embodiment. FIG. 21 is a cross-sectional view illustrating apart of the administration instrument for medical use according to the fifth embodiment. FIG. 22 is a perspective view illustrating an administration instrument for medical use according to another embodiment. FIG. 23 is a cross-sectional view illustrating a part of the administration instrument for medical use shown in FIG. 22.

In FIG. 20, reference numeral 102 denotes a needle insertion attachment, numeral 103 denotes a body of the administration instrument for medical use, numeral 104 denotes a display, numeral 105 denotes an administration amount setting dial, and numeral 106 denotes an injection button. The needle insertion attachment 102 is constructed to be able to slide toward the injection button 106 almost at the same time as a time when the needle 101 is inserted into the skin.

In FIG. 21, the needle insertion attachment 102 is constructed to be shorter than the needle in the longitudinal direction of the needle, and slides when the needle is inserted into the skin, thereby turning on switches (third switches) 109a and 109b that are provided in the body. When the switches 109a and 109b are turned on, the microprocessor 125 judges that the needle is inserted into the skin.

Further, the administration completion detection means is a microprocessor 125 which judges a state where a switch (not shown, corresponding to the switch 113 in FIG. 18 or the switch 413 in FIG. 32 as described in the prior art) is turned on once and turned off again as the completion of the administration. That is, the microprocessor 125 performs the judgment so as to record the amount of the injection administered, and the date and time of the administration in the memory 112 only when the state of the above-mentioned switch (not shown) indicates the completion of the administration while the switches 109a and 109b are ON.

On the other hand, at the air removal, the needle insertion attachment 102 is not operated and the switches 109a and 109b are remained OFF because the air removal is performed in the air with the needle 101 facing upward and the injection button 106 facing downward. Even when the injection button 106 is pressed at this time and the switch 113 is turned ON once and turned OFF again, resulting in the state of the completion of the administration, the microprocessor 125 judges that the histories of the amount of the injection administered, the date, and the time are not to be recorded in the memory because the switches 109a and 109b are OFF. Thus, there is provided an administration instrument for medical use that records the amount of the injection administered, the date, and the time in the memory 122 as the histories only when the needle 101 is actually inserted into the skin and the administration has been completed, and does not record the histories at the air removal operation. In this case, dependent on the shape of the needle insertion attachment, it is possible to detect the insertion of the needle even with one of the switches 109a and 109b.

FIG. 22 is a diagram illustrating an instrument in which these switch 109a and 109b are integrated into one switch. In FIG. 22, numeral 140 denotes a needle insertion detection switch (third switch), numeral 103 denotes a body of the administration instrument for medical use, numeral 104 denotes a display, numeral 105 denotes an administration amount setting dial, and numeral 106 denotes an injection button. The needle insertion detection switch 140 is provided on the same side of a skin touch portion 141 as the needle 101, the portion 141 being provided to stabilize the administration instrument body without wobbling at the administration.

In FIG. 23, the needle insertion detection switch 140 is turned ON almost at the same time as a time when the needle 101 is inserted into the skin. When this needle insertion detection switch 140 is turned ON, the microprocessor 125 judges that the needle is inserted into the skin.

Figure 27:
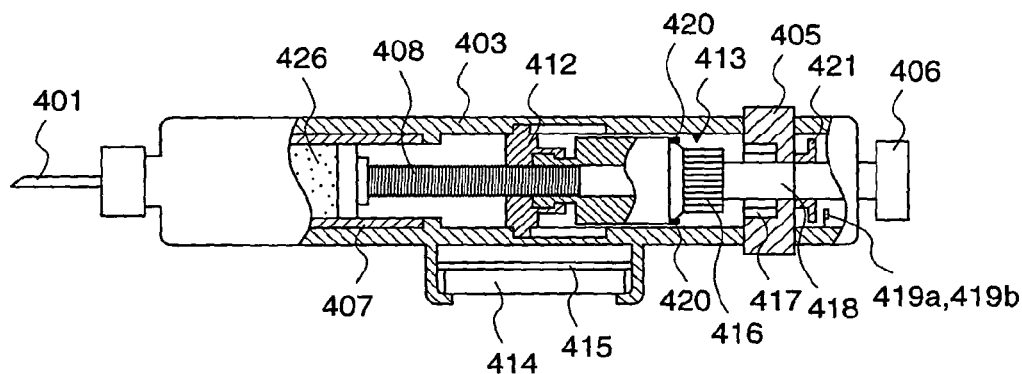
FIG. 27 is a top view illustrating the conventional administration instrument for medical use partially in cross section.
Figure 28:
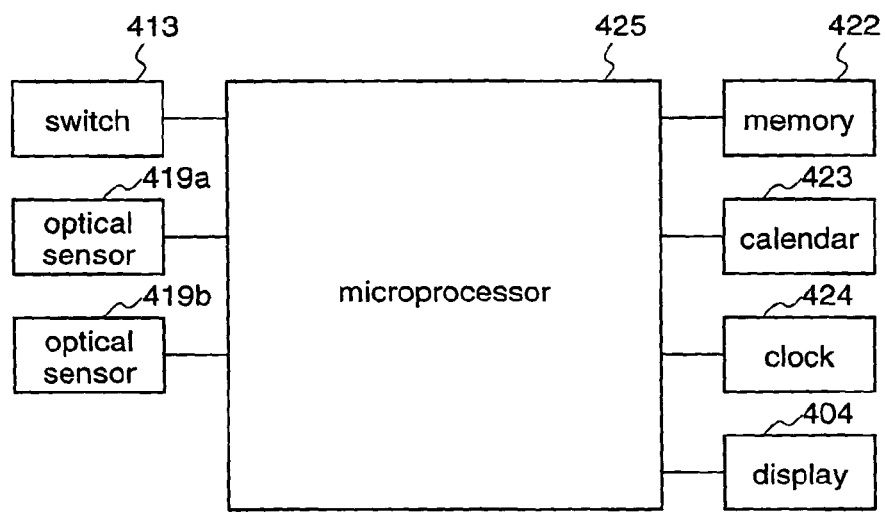
FIG. 28 is a block diagram for explaining the conventional administration instrument for medical use.
Figure 29:
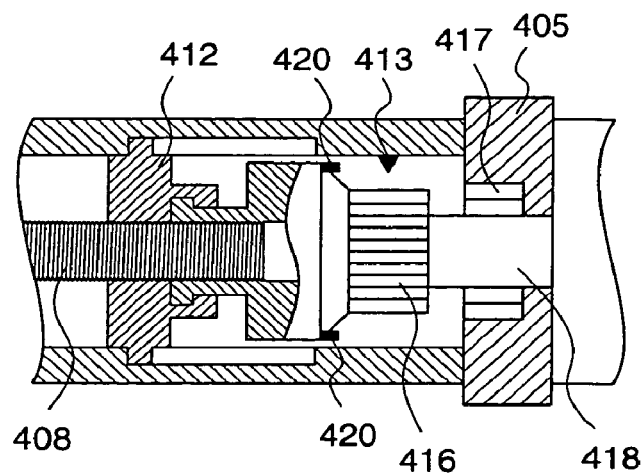
FIG. 29 is a cross-sectional view illustrating a means for detecting completion of administration in the conventional administration instrument for medical use.
Figure 30:
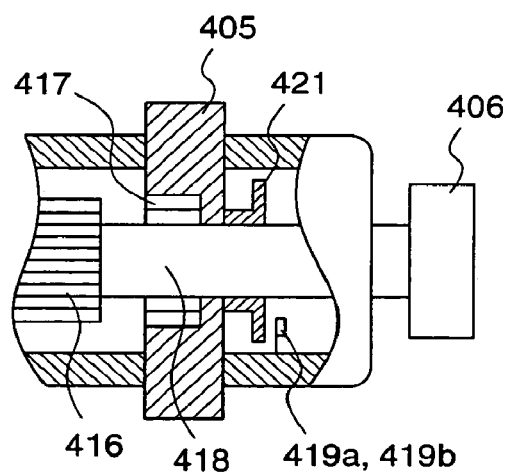
FIG. 30 is a cross-sectional view illustrating a means for detecting the amount of an injection in the conventional administration instrument for medical use.
Figure 31:
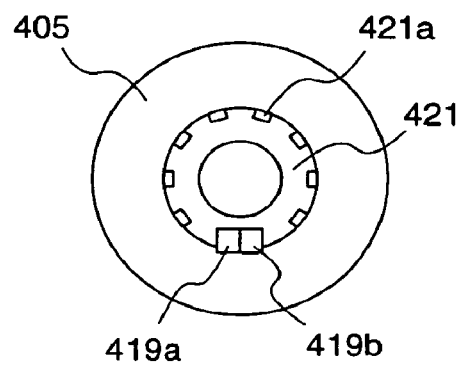
FIG. 31 is a side view illustrating a means for detecting the amount of an injection in the conventional administration instrument for medical use.

Further, the administration completion detection means is the microprocessor 125 that judges a state where the switch 113 in FIG. 19 a switch (not shown in FIG. 19, corresponding to the switch 113 in FIG. 18) is turned ON once and turned OFF again as the completion of the administration, as the switch 413 in FIG. 27 described in the prior art. That is, the microprocessor (control unit) 125 makes the judgment so that the amount of the injection administered, the date, and the time are recorded in the memory (injection amount recording unit) 122 only when the state of the switch 113 the not-shown switch indicates the completion of the administration while the needle insertion detection switch 110 switch 140 is ON.

On the other hand, at the air removal, the needle insertion detection switch 110 switch 140 is OFF because the air removal operation is performed in the air with the needle 101 facing upward and the injection button 106 facing downward. Even when the injection button 106 is pressed at this time, and the switch 113 is turned ON once and turned OFF again, resulting in the state of the completion of the administration, the microprocessor 125 judges that the histories of the amount of the injection, the date, and the time are not to be recorded in the memory 122 because the needle insertion detection switch 110 switch 140 is OFF.

Accordingly, there is provided an administration instrument for medical use which records the amount of the injection administered, the date, and the time in the memory 122 as the history only when the needle is inserted in the skin and the administration has been completed, without recording the history at the air removal operation. In this case, when the position of the needle insertion detection switch 110 is nearer to the needle 101, the detection at a time when the needle 101 is touched to the skin becomes more effective.

This invention is applicable to administration instruments for medical use that are used in performing administration of a drug solution such as an injection, and suitable for alleviating a pain of the administrator as well as performing the administration with stability and with reliability.

The invention claimed is:

1. An administration instrument for medical use, comprising:
  a needle contact detection unit configured to detect that a needle is touching skin;
  an injection completion detection unit configured to detect that injection has been completed;
  an injection amount detection unit configured to detect an amount of the injection administered;
  an injection amount recording unit configured to record the amount of the injection administered; and
  a control unit configured to control the injection amount detection unit and the injection amount recording unit to record the amount of the injection administered only when the injection completion detection unit detects that the injection has been completed and the needle contact detection unit detects that the needle is touching the skin, after an air removal operation has occurred in a state in which the needle contact detection unit does not detect that the needle is touching the skin and the injection amount recording unit does not record the amount of the injection administered.

2. The administration instrument for medical use of claim 1 further comprising:

a calendar unit configured to generate a present date information; and a clock unit configured to generate a present time information; and wherein the control unit is configured to detect that the injection has been completed and, at the same time, record the date and the time of the completion of the injection.

3. The administration instrument for medical use of claim 1 including:

a display unit configured to display an injection amount in setting an amount of the injection to be administered, and an injection amount that is recorded when the injection has been completed.

4. The administration instrument for medical use of claim 3 wherein the display unit is configured to display the date and the time, in addition to the injection amount that is recorded at the completion of the injection.

5. The administration instrument for medical use of claim 1 wherein the needle contact detection unit includes:

a ring-shaped or a semi-ring-shaped contact detection member configured to slide along the needle at an instant when the needle is inserted; and a switch operated by the sliding of the contact detection member.

6. The administration instrument for medical use of claim 1 wherein the needle contact detection unit includes:

a switch on the same side of a skin touch portion as the needle, and operated during the administration at an instant when the needle is inserted into the skin.

* * * * *

UNITED STATES PATENT AND TRADEMARK OFFICE
CERTIFICATE OF CORRECTION

PATENT NO. : 8,287,500 B2
APPLICATION NO. : 12/904508
DATED : October 16, 2012
INVENTOR(S) : Tokumi Baba It is certified that error appears in the above-identified patent and that said Letters Patent is hereby corrected as shown below:

Title Page;

(1) The "Related U.S. Application Data" should be as follows:
   (62)    Division of application No. 10/498,091, filed as application No. PCT/JP02/13055 on December 13, 2002, now Pat. No. 7,922,699.

In the Specification;

Col. 1, lines 4-12;
   (2) The "CROSS-REFERENCE TO RELATED APPLICATION" in the specification should read as follows:

This application is a divisional of U.S. Application No. 10/498,091, filed on June 10, 2004, which is a National Stage application of PCT/JP02/13055, filed on December 13, 2002, the entirety of both of which are incorporated herein by reference.

Signed and Sealed this
Twenty-third Day of April, 2013

Teresa Stanek Rea
*Acting Director of the United States Patent and Trademark Office*